United States Patent [19]
Hughes, Jr. et al.

[11] Patent Number: 6,139,873
[45] Date of Patent: *Oct. 31, 2000

[54] COMBINED PHARMACEUTICAL ESTROGEN-ANDROGEN-PROGESTIN

[75] Inventors: Claude L. Hughes, Jr., Simi Valley, Calif.; Manuel J. Jayo, Advance, N.C.

[73] Assignees: Cedars-Sinai Medical Center, Los Angeles, Calif.; Wake Forest University, Winston-Salem, N.C.

[ * ] Notice: This patent is subject to a terminal disclaimer.

[21] Appl. No.: 09/177,866

[22] Filed: Oct. 23, 1998

Related U.S. Application Data

[63] Continuation-in-part of application No. 09/102,707, Jun. 22, 1998, Pat. No. 5,962,021, which is a continuation of application No. 08/679,764, Jul. 10, 1996, Pat. No. 5,770,226.

[51] Int. Cl.$^7$ .............................. A61K 9/20; A61K 31/56
[52] U.S. Cl. ...................... 424/464; 424/449; 424/443; 424/423; 514/170; 514/841; 514/843
[58] Field of Search .................................... 424/464, 449, 424/423, 443; 514/170, 841, 843

[56] References Cited

U.S. PATENT DOCUMENTS

| | | | |
|---|---|---|---|
| 4,220,599 | 9/1980 | Van Der Vies | 260/397.4 |
| 5,211,952 | 5/1993 | Spicer et al. | 424/426 |
| 5,340,584 | 8/1994 | Spicer et al. | 424/426 |
| 5,595,759 | 1/1997 | Wright et al. | 424/464 |
| 5,770,226 | 6/1998 | Hughes, Jr. et al. | 424/464 |
| 5,962,021 | 10/1999 | Hughes, Jr. et al. | 424/464 |

FOREIGN PATENT DOCUMENTS

92/18107  10/1992  WIPO .

OTHER PUBLICATIONS

The Contraception Report, Baylor College of Medicine, vol. VI, No. 5, Nov. 1995.
Adams et al., "Effects of androgens on coronary atherosclerosis and atherosclerosis-related impairment of vascular responsiveness," Arterioscler. Thromb. Vasc. Biol., 15:562–70, 1995.
Adashi, "The climacteric ovary as a functionalgonadotropin-driven gonadropin-driven androgen-producing gland," Fertil. Steril., 62:20–27, 1994.
Barrett–Connor, "The economic and human costs of osteoporotic fracture," Am. J. Med., 98(Suppl. 2A):3S–8S, 1995.
Bubenik, et al., "The effect of artificial photoperiodicity and antiandrogen treatment on the antler growth and plasma levels of LH, FSH, testosterone, prolactin and alkaline phosphatase in the male white–tailed deer," Comp. Biochem. Physiol. A Comp. Physiol., 87:551–59, 1987.
Buchanan, et al., "Effects of excess endogenous androgens on bone density in young women," J. Clin. Endocrinol. Metab., 67:934–43, 1988.
Carr et al., "Oral contraceptive pills, gonadotropin–releasing hormone antagonists, or use in combination for treatment of hirsutism: A clinical research center study," J. Clin. Endocrin. Metab., 80:1169–78, 1995.
Castro et al., "Ketamine HCl as a suitable anesthetic for endocrine, metabolic, and cardiovascular studies in *Macaca fascicularis* monkeys," Proc. Soc. Exp. Biol. Med., 168:389–94, 1981.
Cauley et al., "Black–white differences in serum sex hormones and bone mineral density," Am. J. Epidemiol., 139:1035–46, 1994.
Clarkson, et al., "Oral contraceptives and coronary artery atherosclerosis of cynomolgus monkeys," Obstet. Gynecol., 75:217–22, 1990.
Colvard, et al., "Identification of androgen receptors in normal human osteoblast–like cells," Proc. Natl. Acad. Sci. USA, 86:864–57, 1989.
DeCherney, "One–sparing properties of oral contraceptives," Am. J. Obstet. Gynecol., 174:1, 1993.
Duhper, et al., "Effects of hormonal status on bone density in adolescent girls," J. Clin. Endocrinol. Metab., 71:1083–88, 1990.
Enzelberger, et al., "Influence of oral contraceptive use on bone density in climacteric women," Maturitas , 9:375–8, 1988.
Flanagan, et al., "Casodex reduces bone formation rate in female rats," (Abstract), J. Bone Miner. Res., 10(Suppl I):S349, 1995.
Fortney, et al., "Bone mineral density and history of oral contraceptive use." J. Reprod Med 39:105–9, 1994.
Frank, "The role of estrogen in pubertal skeletal physiology: epiphyseal maturation and mineralization of the skeleton," Acta Paediatr., 84:627–30, 1995.
Gallagher, et al., "Androgens contribute to the stimulation of cancellous bone formation by ovarian hormones in female rats," American Physiological Society, 270:E407–12, 1996.
Gallagher, et al., "Ovarian transplantation maintains bone formation more effectively than exogenous oestrogen in ovariectomised osteopenic rats," Department of Histopathology, St. George's Hospital Medical School, London. Jan. 96.
Gambacciani, et al., "Longitudinal evaluation of perimenopausal vertebral bone loss: effects of low dose oral contraceptive preparation on bone mineral density and metabolism," Obstet. Gynecol., 83:392–96, 1994.
Garnero, et al., "Decreased bone turnover in oral contraceptive users," Bone, 16(5):499–503, 1995.
Garnero, et al. "Genetic influence on bone turnover in postmenopausal twins," Journal of Clinical Endocrinology and Metabolism, 81(1): 140–6, 1996.

(List continued on next page.)

*Primary Examiner*—James M. Spear
*Attorney, Agent, or Firm*—Timothy S. Corder; Vinson & Elkins LLP

[57] ABSTRACT

Disclosed are methods and compositions for oral contraception and for hormone replacement therapy. Certain compositions of the invention contain androgens, preferably methyltestosterone to be taken in conjunction with estrogens and progestins.

39 Claims, No Drawings

OTHER PUBLICATIONS

Goldsmith and Johnston, "Bone mineral: Effects of oral contraceptives, pregnancy, and lactation," J. Bone J. Surg., 57A:657–68, 1975.

Hickock, et al., "A comparison of esterified estrogens with and without methylestosterone: effects on endometrial histology and serum lipoproteins in postmenopausal women," Obstet. Gynecol., 82:919–24, 1993.

Hreshchyshyn, et al., "Association of parity, breast–feeding, and birth control pills with lumbar spine and femoral neck bone densities," Am. J. Obstet. Gynecol. 159:318–22, 1988.

Hughes, et al., "Reproductive hormone levels in gynecologic oncology patients undergoing surgical castration after spontaneous menopause," Gynecol. Oncol, 40:42–5, 1991.

Jayo, et al., "Bone mass in female cynomolgus macaques: A cross–sectional and longitudinal study by age," Calcif. Tissue Int., 54:231–6, 1994.

Jayo, et al., "Accuracy and precision of lumbar bone mineral content by dual–energy X–ray absorptiometry in live female monkeys," Calcif. Tissue Int., 49:438–40, 1991.

Jayo, et al., "Effects of thiazide and estrogen on bone in ovariectomized monkeys," (Abstract), J. Bone Miner. Res., 10:S256, 1995.

Jayo, et al., "Anthropometry and bone mineral status in endocrinologically manipulated female cynomolgus macaques (*Macaca fascicularis*)," (Abstract), J. Bone Miner. Res., 4(Suppl. 1):S181, 1989.

Jayo, et al., "Effects on bone of surgical menopause and estrogen therapy with our without progesterone replacement in cynomolgus monkeys," Am. J. Obstet. Gynecol., 193:614–18, 1990.

Jayo, et al., "Cross–Sectional Examination of Lumbar Bone Mineral by Dual Energy X–Ray Absorptiometry (DXA) in Female Cynomolgus Macaques" S170 (Abstr. #348). Feb. 1990.

Jerome, et al., "Bone functional changes in intact, ovariectomized, and ovariectomized, hormone–supplemented adult cynomolgus monkeys (*Macaca fascicularis*) evaluated by serum markers and dynamic histomorphometry," J. Bone Miner. Res., 9:527–40, 1994.

Johnell and Nilsson, "Life–style and bone mineral mass in perimenopausal women." Calcif. Tissue Int., 36:354–56, 1984.

Kanders, et al., "Interaction of calcium nutrition and physical activity on bone mass in young women," J. Bone Miner. Res., 3:145–49, 1988.

Kanis, "Treatment of osteoporosis in elderly women," Am. J. Med., 98(Suppl. 2A):605–65, 1995.

Kasperk, et al., "Studies of the mechanism by which androgens enhance mitogenesis and differentiation in bone," J. Clin. Endocrinol. Metab., 71:1322–29, 1990.

Kasra and Grynpas, "The effects of androgens on the mechanical properties of primate bone," Bone, 17:265–70, 1995.

Polatti, et al., "Bone mass and long–term monophasic oral contraceptive treatment in young women," Contraception, 51:221–24, 1995.

Raisz, et al., "Comparison of the effects of estrogen alone and estrogen plus androgen on biochemical markers of bone formation and resorption in postmenopausal women," Journal of Clinical Endocrinology and Metabolism, 81(1):37–43, 1996.

Riasz, "The role of androgens in the pathogenesis and treatment of postmenopausal osteoporosis," The Female Patient, 11–18, 1996.

Recker, et al., "Bone gain in young adult women," JAMA, 268:2403–08, 1992.

Register, et al., "Oral contraceptive treatment inhibits normal bone mineral accretion and bone metabolism in young adult female macaques," (Abstract), J. Bone Min. Reser., 10(Suppl 1):S356, 1995.

Register, et al., "Oral Contraceptive Treatment Inhibits the Normal Acquisition of Bone Mineral in Skeletally Immature Young Adult Female Monkeys," Osteoporosis Int. 1997.

Ribot, et al., "Late consequences of a low peak bone mass," Acta. Paediatr. Suppl., 411:31–5, 1995.

Shargil, "Hormone replacement therapy in perimenopausal women with a triphasic contraceptive compound: A three year prospective study." Int. J. Fertil. 30(1):15–28, 1985.

Shively, et al., "Body fat distribution as a risk factor for coronary artery atherosclerosis in female cynomolgus monkeys," Arteriosclerosis, 7:226–31, 1987.

Simberg, et al., "High bone density in hyperandrogenic women: effect of gonadotropin–releasing hormone agonist alone or in conjunction with estrogen–progestin replacement," Journal of Clinical Endocrinology and Metabolism, 81(2):646–51, 1996.

Slemenda, et al., "Sex steroids, bone mass, and bone loss," J. Clin. Invest., 97(1):14–21, 1996.

Soule, et al., "Osteopenia as a feature of the androgen insensitivity," Clinical Endocrinology, 43:671–75, 1995.

Stevenson, et al., "Determinants of bone density in normal women: Risk factors for future osteoporosis?," Br. Med. J., 298:924–8, 1989.

Teegarden, et al., "Effect of exercise intervention and oral contraceptive use on spine bone mineral density in young women," (Abstract), J. Bone Miner. Res., 10(Suppl. 1):S456, 1995.

Tulli, et al., "Immunocytochemical method for the simultaneous demonstration of three proteins in EDTA decalcified, paraffin embedded bone sections," J. Histotechnol., 15:93–7, 1992.

Tuppurainen, et al., "The effect of previous oral contraceptive use on bone mineral density in perimenopausal women," Osteoporosis International, 4:93–8, 1994.

Vanin, et al., "Androgens and bone density in the aged ovariectomized rat," (Abstract), J. Bone Miner. Res., 10(Suppl. 1):S250, 1995.

Watts, et al., "Comparison of oral estrogens and estrogens plus androgen on bone mineral density, menopausal symptoms, and lipid–protein profiles in surgical menopause," Obstet. Gynecol., 85:529–37, 1995.

Wiegratz, et al., "Effect of two oral contraceptives containing ethinyl estradiol and gestodene or norgestimate upon androgen parameters and serum binding proteins," Contraception, 51:341–6, 1995.

Wiren, et al., "Homologous regulation of the androgen receptor in human osteoblastic cells," (Abstract), J. Bone Miner. Res., 10(Suppl. 1):S494, 1995.

PCT Search Report mailed Sep. 15, 1997.

Ursin et al., "Contraception and Cancer Prevention," Advances in Contraceptive Delivery Systems 10(3–4):369–86, 1994.

Supplementary European Search Report, Jul., 1999.

COMBINED PHARMACEUTICAL ESTROGEN-ANDROGEN-PROGESTIN

This application is a continuation-in-part of copending U.S. Ser. No. 09/102,707 filed on Jun. 22, 1998 U.S. Pat. No. 5,962,021, which is a continuation of U.S. Ser. No. 08/679,764 filed Jul. 10, 1996, now U.S. Pat. No. 5,770,226, the entire contents of which are incorporated herein by reference.

BACKGROUND OF THE INVENTION

1. Field of the Invention

The present invention relates generally to the field of pharmaceutical preparations and in particular to the field of oral contraceptives and hormone replacement therapy. In particular the present invention addresses the field of peak bone mass accrual in young oral contraceptive users and restoration of normal hormonal balance in women of any age in need thereof.

2. Description of the Related Art

Due to the relatively high rate of teenage pregnancy in the United States, pediatric and adolescent gynecologists often recommend that young women take some form of contraception to prevent unwanted pregnancies (The Contraception Report, 1995). The most common method of contraception among adolescents is oral contraceptives, taken by approximately 46% of the sexually active population. Consequently, almost half of all premenopausal women (<44 years) are potentially taking oral contraceptives while their skeleton is still maturing and before reaching peak bone mass, which occurs at about age 30–35. Peak bone mass is a term that describes a point at which the maximum bone density is reached. For a woman, bone density increases until about age 30–35, and then slowly decreases for the remainder of her life. This peak is known as the peak bone mass. As the bone density decreases in later years, osteopenia and osteoporosis with bone fractures are more likely to occur. It is important, therefore, to forestall these problems by attaining as high a peak as possible.

Although estrogen is necessary for maintaining bone density in premenopausal women, the role of androgens or their combined effect is unclear. It is generally accepted that low-dose estrogens are potent bone growth promoters and probably provide the major growth stimulus in girls, while in boys, estrogens may be involved in the growth spurt along with testosterone (Kulin, 1991). However, some recent evidence suggests that androgens play an important role in building and maintaining bone in the female as well as in the male. During puberty, androgens influence bone growth and peak bone mass, but after puberty, during adolescence and early adulthood, androgens are also involved in the maintenance of bone mass. Peak bone mass is acquired by age 30–35 (Recker, et al., 1992), but 15% of the adult height and 48% of the skeletal mass are attained during adolescence.

Oral contraceptive treatment, like oophorectomy, causes a significant decrease in androgen levels and consequently oral contraceptives are commonly used to treat hirsutism in women (Carr, et al., 1995). Young women with hyperandrogenemia show increased levels of luteinizing hormone (LH) and free testosterone to total testosterone ratio (fT)/T, and a decreased serum level of sex hormone-binding globulin (SHBG). Low-dose oral contraceptives reduce the hormone imbalance and hyperandrogenemia (Yamamoto and Okada, 1994; Rosenfield and Lucky, 1993). Interestingly, not only does oral contraceptive therapy lower serum A, T and fT in hyperandrogenic women, but estradiol (E2) levels also significantly decrease with oral contraceptive therapy.

Among the first orally active steroids to be used in inhibiting ovulation, some had inherent estrogenic activity and some preparations of progestins were later found to be contaminated with estrogen. This suggested that estrogen enhanced the suppressive effect of the progestin and led to the general use of a mixture of the two. A comprehensive investigation of the inhibition of ovulation by the use of progestational agents was initiated by Rock, Pincus, and Garcia. The study showed that ovulation could be abolished at will for as long as desired and with great regularity (Rock et al, 1957; Pincus, 1960). The compounds used were derivatives of 19-nortestosterone, given by mouth from day 5 to day 25 of the menstrual cycle (the first day of menses is day 1).

The most common type of oral contraceptive is the combination preparation, which contains both an estrogen and a progestin. Experience with these preparations shows them to be 99 to 100% effective. This method of reversible contraception is, then, the most effective yet devised. Other modifications of steroidal contraception have also been tried with success. Sequential preparations, in which an estrogen is taken for 14 to 16 days and a combination of an estrogen and a progestin is then taken for 5 or 6 days, have been about 98 to 99% successful as oral contraceptives. However, because of reports suggesting an increased incidence of endometrial tumors and a lower efficacy, sequential preparations of this type have been removed from th e market. They have been replaced by products that contain estrogen and relatively low amounts of a progestin that varies during the monthly cycle. Biphasic and triphasic formulations of sequential preparations of oral contraceptives are listed in Table 1. These preparations have been developed in attempts to lower the total amounts of hormone given and thus to reduce the incidence and severity of side effects.

The relationship between oral contraceptive use and skeletal health ha s been examined in a number of human studies. Tuppurainen, et al. (1994) studied the effects of oral contraceptive use on BMD in perimenopausal women (48–60 years). Twenty-nine percent of the women were past users of or al contraceptives. Oral contraceptive users (n=939) had a slightly higher (but statistically significant) lumbar BMD than non-users (n=2283). The study with the largest number of subjects (the Oral Contraception Study of the Royal College of General Practitioners, n=46,000 women) was carried out between 1968 and 1990 and examined the relationship between oral contraceptive use and subsequent incidence of first fractures (excluding skull, rib, and multiple fractures) in married or living as married women (Cooper, et al., 1993). After adjustment for age, parity, cigarette smoking, and socioeconomic class, women who had ever used oral contraceptives were found to be at significantly higher risk for subsequent fractures (relative risk 1.20) compared to women who had never used oral contraceptives. Thus, this very large prospective study suggests that oral contraceptive use does not promote long term skeletal health and may even be detrimental in terms of fracture risk.

While the majority of studies in humans have utilized female populations with age ranges well into the postmenopausal years, a few studies have focused on "younger" females who have not yet attained peak bone mass. In a longitudinal study of 156 premenopausal women aged 20–30, Recker, et al. (1992) found a positive association between oral contraceptive use and whole body bone mass, but no association with lumbar spine (L2-L4) or forearm bone mass. Lindsay, et al. (1986) reported results from 2 cross-sectional studies, one of which involved 57 healthy premenopausal women between 25 and 35 years of age, 24 of which had previously taken oral contraceptives (30 or 50 mg ethinyl estradiol along with norgestrel) for more than 6 months. None of the subjects was taking oral contraceptives at the time of the study. Previous oral contraceptive use was associated with increased BMD in the lumbar spine but not in the radius. The second cross-sectional study showed no association between oral contraceptive use on lumbar spine BMD in 14 postmenopausal women compared to 24 age-matched controls.

In a cross-sectional study of 60 women aged 24–35, Kanders, et al. (1984) found that oral contraceptive users (greater than 5 months use) had a significantly higher spinal BMD than non-users. Goldsmith and Johnston (1975) examined the relationship between oral contraceptive use and distal radius bone mineral among different populations of women in a large cross-sectional study carried out in 1969 and 1970, when most of the oral contraceptive users aged 20–29 were taking mestranol (n=219) and relatively few were taking ethinyl estradiol (n=47). High dose mestranol use (>100 mg/day) was associated with increased radial bone mass, while ethinyl estradiol (50 or 100 mg/day) use and radial bone mass were not associated in white women (n=65) and were negatively associated in black women (n=11).

Stevenson, et al (1989) found no association between oral contraceptive use and bone density at several sites, including lumbar spine, in 112 premenopausal women aged 21–52 (median age=34.1). However, positive associations were found between bone density at these same sites and oral contraceptive use in 172 postmenopausal women aged 28–68 (median age=53.4). Mazess and Barden (1991) found no relationship between oral contraceptive use and BMD of the spine, radius, or femoral neck in a study of 200–300 healthy women of 20–39 years of age. Recently, Hansen (1994) studied 249 healthy premenopausal women aged 21 to 51 (17 were <30 years of age) and reported no association of oral contraceptive use with bone density at a number of skeletal sites, although a significant reduction (<32%) in BGP was observed in current oral contraceptive users compared to never users.

In a recent study, young women using oral contraceptives did not gain spinal bone density over time (Carr, et al., 1995). According to their reported age (mean age of 26±1 yr) and using regression lines reported by Recker, et al (1992), bone mass in most of the women in this study should have been increasing during the study period, ending with a positive balance. Also, Teegarden, et al. (1995), investigated the interaction between oral contraceptive use and exercise in women ages 18 to 31 years. Surprisingly, after 6 months, women who were exercising and using oral contraceptives lost a significant amount of spinal bone mineral density (BMD), whereas women not exercising and taking oral contraceptives gained a significant amount of spinal BMD. Serum concentrations of hormones were not reported (Teegarden, et al., 1995). These results suggest serious consequences. If young women who exercise and take oral contraceptives fail to gain bone during their adolescent and young adult years (ages 15 to 30 years), they will attain a lower than expected peak bone mass. Therefore, age-related and postmenopausal bone loss will have a greater effect on bone mass and a fracture threshold may be reached earlier in life.

Another area of need, in relation to hormonal therapies, is in the mature population of women who take estrogens, and/or progestins for birth control, and/or for hormone replacement therapy (HRT) for women undergoing menopause, or without functioning ovaries. This group would include premenopausal, perimenopausal and postmenopausal women. There is a need, for example, for a therapy that would prevent pregnancy in women undergoing menopause, that would also alleviate at least some of the symptoms of menopause. An added benefit of such a product would be an increase in the psychological well being, the libido, and sexual function in this population.

One effect of estrogen supplementation is an increase in sex hormone-binding globulin (SHBG) (Raisz et al., 1996), which has been reported to increase up to 200 to 240% in women given a combination of ethinyl estradiol and a progestin (Wiegratz et al., 1995). Sex hormone-binding globulin is a serum protein that binds both testosterone and 17β-estradiol, a nd this binding affects the biological availability of those hormones. Therefore, the increase in SHBG, that occurs with estrogen and progestin supplementation results in lower levels of free androgens and estrogens, both of which bind to SHBG, and higher levels of estrogens have to be administered in order to achieve the desired biological activity. The ideal therapy would counteract th is SHBG effect so that the benefits of estrogen/progestin therapy could be achieved at lower hormone supplementation levels.

There is an immediate need therefore, for an oral contraceptive, especially for women in their teens and twenties, that is effective to prevent unwanted pregnancies and still allows the attainment of normal peak bone mass. There is also a need for a hormone replacement therapy regimen that counteracts the SHBG effect. Such a regimen would achieve the beneficial effects of estrogen therapy at lower estrogen levels, t hu s decreasing the probability of deleterious side effects such as thromboembolic disease and breast cancer.

SUMMARY OF THE INVENTION

The present disclosure, in a general sense, includes novel compositions and methods for oral contraception and hormone replacement therapy. These compositions and methods provide improvements over prior methods of oral contraception and hormone replacement therapy in that a combination of three hormones, an androgen, an estrogen and a progestin is included in certain of the formulations. This combination offers benefits not found in prior art compositions that include only one or two of these hormones. Those benefits include maximizing bone accrual in younger users of oral contraceptives, the ability to achieve the desired biological activity of estrogen therapy at lower dosages, the endometrium protective and antiovulatory effects of progestins, and the physical and psychological benefits of androgens.

The compositions described herein are, in certain broad aspects, contraceptive preparations comprising estrogen and progestin and an androgen in an amount effective to maximize bone accretion in a user of oral contraceptives. In certain compositions, the androgen is present in an amount effective to decrease the level of SHBG in the blood of a user of estrogen/progestin supplements, thus decreasing the amount of estrogen necessary to achieve the desired biological activity. The androgen may be any androgen known in the art that is suitable for use in an oral contraceptive preparation or hormone replacement therapy and is preferably a testosterone and more preferably methyltestosterone. Representative androgens that are currently available are shown in Table 2. It is understood that any of these formulations that are adaptable to an oral contraceptive or hormone replacement therapy would be useful in the practice of the present invention. It is also understood that the use of the androgen, estrogen, and progestin compositions described herein may be formulated for administration in any suitable form, such as orally, as an implant or bolus injection, as a topical or vaginal ointment, or as a transdermal patch, for example.

The dosage will depend upon the physiological reaction of the subject to the compositions, and will be monitored by the prescribing physician. For example, certain subjects such as athletes, for example, may require that their serum testosterone levels not be increased above normal physiological levels. Therefore, the physician may monitor serum androgens over periods of about every three months, for example, to determine the correct level of testosterone to include in the oral contraceptive or HRT formulation. It is contemplated that the contraceptive formulations may be available in three or more levels of all three hormones, and that the physician would prescribe a higher or lower androgen formulation depending on changes in serum testosterone levels in users of the formulations. It is also contemplated that the hormone replacement compositions may be available in five or more formulations in order to give the physician more choices in finding the best therapy for a particular patient.

Certain formulations of the invention will contain from about 0.2 milligrams to about 1.5 milligrams methyltestosterone or the equivalent per daily dose. The formulations may contain for example, about 0.2, 0.3, 0.4, 0.5, 0.6, 0.7, 0.8, 0.9, 1.0, 1.1, 1.2, 1.3, 1.4 or 1.5 milligrams methyltestosterone per daily dose. The use of the term "about" in the present disclosure means "approximately," and use of the term indicates that dosages slightly outside the cited ranges may also be effective and safe, and such formulations are also encompassed by the scope of the present claims. The preparations containing methyltestosterone are preferably administered during days 8–13 of a menstrual cycle to correspond with naturally occurring increases in testosterone levels during the menstrual cycle when the formulations are used for contraception. For example, it is known that testosterone and estrogen levels both increase during this period of the normal cycle. The androgen or testosterone containing compositions also preferably contain an estrogen and a progestin for the prevention of conception. Preferably, the progestin is levonorgestrel, or the equivalent, present in a concentration of from about 0.025 to about 0.150 milligrams, and would include 0.025, 0.050, 0.075, 0.10, 0.125 and 10 0.150 milligram levonorgestrel equivalents per daily dose. The estrogen may be ethinyl estradiol or the equivalent present at a concentration of from about 0.005 to about 0.035 milligrams ethinyl estradiol equivalent per daily dose, and would include, for example, 0.005, 0.01, 0.015, 0.02, 0.025, 0.03, or 0.035 micrograms of ethinyl estradiol or the equivalent per daily dose.

An embodiment of the present invention may be described as an oral contraceptive preparation comprising a first composition comprising methyltestosterone with levonorgestrel and ethinyl estradiol to be administered daily from day 8 to about day 13 of a menstrual cycle. The contraceptive preparation also contains a second composition comprising levonorgestrel and ethinyl estradiol to be administered daily from day 14 to about day 18 following administration of the first composition. The preparation may also be defined as containing a third composition comprising levonorgestrel and ethinyl estradiol to be administered daily following administration of the second composition from about day 19 until about day 28 of a menstrual cycle. This preparation may further comprise a placebo composition to be taken during days 1–7 of the menstrual cycle. It is understood that the compositions are preferably taken on days 8–13 for the first composition, days 14–18 for the second composition, and days 19–28 for the third composition. However, the timing of administration is understood to be the best time to administer these formulations and may be varied slightly without violating the scope and spirit of the present invention. The first composition may be further defined as comprising from about 0.2 milligrams to about 1.5 milligrams methyltestosterone per daily dose, from about 0.025 to about 0.15 milligrams of levonorgestrel and from about 0.005 to about 0.035 milligrams ethinyl estradiol per daily dose. The second composition may preferably be defined as about 0.075 milligrams levonorgestrel and about 0.04 milligrams ethinyl estradiol per daily dose. The third preparation may be further defined as about 0. 125 milligrams levonorgestrel and about 0.03 milligrams ethinyl estradiol per daily dose.

The invention may also be described in certain embodiments as an oral contraceptive composition comprising from about 0.2 milligrams to about 1.5 milligrams methyltestosterone per daily dose, from about 0.025 to about 0.15 milligrams of levonorgestrel and from about 0.005 to about 0.035 milligrams ethinyl estradiol per daily dose. In certain embodiments the invention may be described as an oral contraceptive composition formulated as 28 tablets as follows: six tablets comprising about 0.2 milligrams to about 1.5 milligrams methyltestosterone, about 0.05 milligrams levonorgestrel, and about 0.03 milligrams ethinyl estradiol; 5 tablets comprising about 0.075 milligrams levonorgestrel, and about 0.04 milligrams ethinyl estradiol; and 10 tablets comprising about 0.125 milligrams levonorgestrel, and about 0.03 milligrams ethinyl estradiol, and the composition may further comprise about 7 placebo tablets. It is understood that the placebo tablets of any of the compositions described herein may contain iron, calcium, vitamins, minerals, or other beneficial supplements to be added to the diet of the oral contraceptive user.

A method of enhancing bone accrual in a subject taking estrogen containing oral contraceptives wherein the subject has not obtained peak bone mass is also an embodiment of the present invention. The method comprises administering an androgen to the subject in conjunction with the oral contraceptives. In preferred embodiments of the method the androgen is administered as about 0.2 milligrams to about 1.5 milligrams of methyltestosterone per day for days 8–13 of the menstrual cycle. The invention may also be described as a method of preventing conception in a subject. The method comprises administering to the subject a formulation comprising about 0.2 milligrams to about 1.5 milligrams methyltestosterone, about 0.05 milligrams levonorgestrel, and about 0.005 to about 0.035 milligrams ethinyl estradiol daily on days 8–13 of the menstrual cycle, then about 0.05 milligrams levonorgestrel and about 0.005 to about 0.04 milligrams ethinyl estradiol daily on days 14–18 of the menstrual cycle, and about 0.125 milligrams levonorgestrel and about 0.03 milligrams ethinyl estradiol daily on days 19–28 of the menstrual cycle.

An embodiment of the present invention may be described as a one month oral contraceptive pack comprising a first composition of 7 tablets comprising a placebo composition to be taken daily on days 1 to 7 of a menstrual cycle. The one month oral contraceptive pack also comprises a second composition of 6 tablets comprising about 0.2 mg to about 1.5 mg methyltestosterone, about 0.050 mg levonorgestrel. and about 0.005 to about 0.035 mg ethinyl estradiol to be taken daily on days 8–13 of a menstrual cycle.

The one month oral contraceptive pack may be further defined as comprising a third composition of 5 tablets comprising about 0.075 mg levonorgestrel and about 0.005 to about 0.040 mg ethinyl estradiol to be taken daily on days 14–18 of a menstrual cycle. The oral contraceptive pack may comprise a fourth composition of 10 tablets comprising about 0.125 mg levonorgestrel and about 0.005 to about 0.035 mg ethinyl estradiol to be taken daily on days 19–28 of a menstrual cycle. The one month pack further comprising a dispenser comprising 28 compartments, each compartment containing an oral contraceptive composition. A typical dispenser would provide for 28 pills to be taken one a day in a determined order. Exemplary dispensers are those described in U.S. Pat. No. 4,165,709, U.S. Pat. No. 4,807,757, U.S. Pat. No. 3,678,884 or U.S Pat. No. 3,651,927 (each incorporated herein by reference).

In other embodiments the present invention comprises a one month oral contraceptive pack comprising a first composition of 7 tablets comprising a placebo composition to be taken daily on days 1 to 7 of a menstrual cycle. The one month oral contraceptive pack also comprises a second composition of 6 tablets comprising about 0.2 mg to about 1.5 mg methyltestosterone, about 0.050 mg levonorgestrel and about 0.030 mg ethinyl estradiol to be taken daily on days 8–13 of a menstrual cycle. The one month oral contraceptive pack may be further defined as comprising a third composition of 5 tablets comprising about 0.075 mg levonorgestrel, about 0.040 mg ethinyl estradiol and about 0.2 mg to about 0.5 mg methyltestosterone to be taken daily on days 14–18 of a menstrual cycle. The oral contraceptive pack may comprise a fourth composition of 10 tablets comprising about 0.125 mg levonorgestrel, about 0.03 0 mg ethinyl estradiol and about 0.2 mg to about 0.5 mg methyltestosterone to be taken daily on days 19–28 of a menstrual cycle. The one month pack further comprising a dispenser comprising 28 compartments, each compartment containing an oral contraceptive composition.

Further embodiments of the invention include formulations for use in hormone replacement therapy. These formulations will include an estrogen, a progestin, and an androgen in various concentrations. As in known in the art of hormone replacement, one may administer estrogens and progestins sequentially. For example, one may administer a progestin on a daily basis, and concurrently administer an estrogen for a certain period (25–120 days, for example) followed by a period of a few days without estrogen and then repeat the cycle. Other dosage regimens might involve 1 to 4 days of a higher estrogen dosage followed by 1–4 days of a higher progestin dosage. Alternatively, one might administer an estrogen and a progestin continuously at a constant level. An aspect of the present invention is the inclusion of an androgen, and in certain embodiments daily androgen doses with any such formulation that includes an estrogen.

Formulations for hormone replacement therapy may be provided in a number of combinations of hormone dosages. For example, such formulations may include androgens, such as methyltestosterone in concentrations of 0.1, 0.2, 0.3, 0.4, 0.5, 0.6, 0.7, 0.8, 0.9, 1.0, 1.1, 1.2, 1.3, 1.4 or 1.5 milligrams or the equivalent per daily dose for example. The formulations may also include a progestin such as levonorgestrel in concentrations of 0.025, 0.05, 0.075, 0.1, 0.125, or 0.150 milligrams or the equivalent per daily dose, and an estrogen such as ethinyl estradiol in concentrations of 0.005, 0.01, 0.015, 0.02, 0.025, 0.03, or 0.035 milligrams or the equivalent per daily dose. These hormonal components of the formulations may be combined to offer a physician flexibility in treating a patient. Preferred formulations may include combinations of 0.25, 0.5, 0.75, 1.0, or 1.25 mg of methyltestosterone; 0.05, 0.1, or 0.15 mg levonorgestrel; and 0.005, 0.01, 0.02 or 0.03 mg ethinyl estradiol per dose. More preferred combinations include the following six combinations of ethinyl estradiol (EE, in $\mu$g): levonorgestrel (LNG, in $\mu$g): and methyltestosterone (MT, in mg):

EE:LNG:MT
5:25:0.25;
5:50:0.5;
10:50:0.5;
10:100:1.0;
20:100:0.5; and
20:100:1.0.

As described herein, by addition of an androgen to a hormonal formulation containing an estrogen, the same effective level of estrogen can be achieved with a smaller dosage. It is understood that higher levels of an androgen, such as methyltestosterone (MT), for example, will compete with an estrogen for binding to sex hormone binding globulin (SHBG), and will also suppress the level of SHBG released into the serum by the liver. As described herein, supplementation with estrogen has been shown to increase the SHBG levels by as much as 200 to 240%. Therefore, preventing this effect by including an androgen or a testosterone in the supplement is contemplated to reduce the estrogen requirement by as much as 50 to 60%, because of the reduced SHBG level compared to supplementation with estrogen and progestin without testosterone. In addition, testosterone competitively binds t o SHBG with higher affinity than estrogen, further reducing the bound estrogen and making it more biologically available. As described, estrogen bound to SHBG is not biologically available. Therefore, supplementation with MT allows lower estrogen dosages to achieve the same effect. Provided herein, therefore, are compositions in which the androgen and estrogen conentrations are varied to achieve the desired biological results while using a lower estrogen supplement than is possible without the addition of testosterone.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described.

DETAILED DESCRIPTION OF THE PREFERRED EMBODIMENTS

It is an object of the present disclosure to provide pharmaceutical compositions and methods of use that would allow a practitioner to treat the hormonal balance of a patient from her earliest use of contraceptives throughout her fertile years, and through menopause and beyond, as well as to provide compositions for any female with a malfunctioning or non-functioning ovary. The present invention provides oral contraceptives that prevent unwanted pregnancies and allow the normal accrual of bone mass in younger users of the contraceptives, so that optimal peak bone mass may be reached by those users. By manipulation of the estrogen/androgen dosages, the disclosed formulations may also continue to prevent conception in older users in need thereof while maintaining a proper estrogen/androgen balance, and continue to provide the proper hormonal balance through menopause and into the postmenopausal years. Throughout the period of use, the present formulations also provide the ovulation preventing, and endometrium protecting effects of progestins.

The present invention arises from the discovery that oral contraceptives prevent the proper accrual of bone in young non-human female primates and that this effect can be attributed to suppression of endogenous androgen levels. This animal study strongly suggests that the same adverse effect occurs in young women (age 15 to 30 years) and due to the same mechanism (suppressed androgen levels). Diminish ed accrual of bon e prevents attainment of maximal peak bone mass, thus increasing the risk of osteoporosis later in life. The problem of poor accrual of bone mass in young women is presently caused by standard oral contraceptive preparations that contain estrogen and progestin. The compositions of the present invention include androgen in addition to estrogen and progestin, and thus offer the unique advantage of allowing normal bone accretion and the attainment of normal peak bone mass.

Preparations and Dosage of Estrogen/Progestin Oral Contraceptives.

Some formulations presently used as oral contraceptives are listed in Table 1. The combined preparations contain 0.02 to 0.05 mg of ethinyl estradiol or mestranol and various amounts of a progestin, and are taken for 21 days. The next course is started 7 days after the last dose or 5 days after the onset of the menstrual flow. It should be noted that ethinyl estradiol is approximately twice as potent as mestranol.

Sequential preparations are formulated to be taken in two (biphasic) or three (triphasic) continuous phases. With biphasic preparations a fixed-dose combination of an estrogen and progestin is taken for 10 days, followed by a different fixed-dose combination of estrogen and progestin for 11 days. The pills are discontinued for 7 days before the cyclic administration is resumed. Triphasic preparations contain the same or different quantities of an estrogen and variable quantities of a progestin in three sets of tablets. Each set is taken for 5 to 10 days, depending upon the specific formulation. After 21 days of administration, the medication is discontinued for 7 days before the cycle is resumed.

TABLE 1

COMPOSITION AND DOSES OF SOME ORAL CONTRACEPTIVES

| ESTROGEN (mg) | PROGESTIN[1] (MG) | REPRESENTATIVE TRADE NAME |
|---|---|---|
| Combinations[2]: | | |
| 0.02 Ethinyl estradiol | 1.0 Norethindrone acetate | LOESTRIN 1/20 |
| 0.03 Ethinyl estradiol | 0.3 Norgestrel | LO/OVRAL |
| 0.03 Ethinyl estradiol | 1.5 Norethindrone acetate | LOESTRIN 1.5/30 |
| 0.03 Ethinyl estradiol | 0.15 Norethindrone acetate | NORDETTE |
| 0.035 Ethinyl estradiol | 0.4 Norethindrone | OVCON35 |
| 0.035 Ethinyl estradiol | 0.5 Norethindrone | BREVICON |
| 0.035 Ethinyl estradiol | 1.0 Ethynodiol diacetate | DEMULEN 1/35 |
| 0.035 Ethinyl estradiol | 1.0 Norethindrone | ORTHO-NOVUM 1/35 |
| 0.05 Mestranol | 1.0 Norethindrone | ORTHO-NOVUM 1/50 |
| 0.05 Ethinyl estradiol | 0.5 Norgestrel | OVRAL |
| 0.05 Ethinyl estradiol | 1.0 Ethynodiol diacetate | DEMULEN 1/50 |
| 0.05 Ethinyl estradiol | 1.0 Norethindrone | OVCON50 |

TABLE 1-continued

COMPOSITION AND DOSES OF SOME ORAL CONTRACEPTIVES

| ESTROGEN (mg) | PROGESTIN[1] (MG) | REPRESENTATIVE TRADE NAME |
|---|---|---|
| 0.05 Ethinyl estradiol | 1.0 Norethindrone acetate | NORLESTRIN 1/50 |
| 0.05 Ethinyl estradiol | 2.5 Norethindrone acetate | NORLESTRIN 2.5/50 |
| Sequentials[3]: | | |
| 0.03, 0.04, 0.03 Ethinyl estradiol | 0.05, 0.075, 0.125 Levonorgestrel | TRI-LEVLEN TRI-NORINYL |
| 0.035 Ethinyl estradiol | 0.5, 1.0, 0.5 Norethindrone | ORTHO-NOVUM 7/7/7 |
| 0.035 Ethinyl estradiol | 0.5, 0.75, 1.0 Norethindrone | ORTHO-NOVUM 10/11 |
| 0.035 Ethinyl estradiol | 0.5, 1.0 Norethindrone | |
| "Minipills"[4]: | | |
| | 0.35 Norethindrone | MICRONOR |
| | 0.075 Norgestrel | OVRETTE |
| Postcoital[5]: | | |
| Diethylstilbestrol | | |

[1]Of the progestin used, norgestrel is somewhat androgenic, while the others have minimal androgenic activity.
[2]Combination tablets are taken for 21 days and are omitted for 7 days. These preparations are listed in order of increasing content of estrogen.
[3]These preparations include fixed-dose tablets with the same or different amounts of estrogen and variable amounts of progestin. With biphasic preparations, the first set of tablets is taken for 10 days and the second for 11 days, followed by 7 days of no medication. With triphasic preparations, each set of tablets is taken for 5 to 10 days in three sequential phases, followed by 7 days of no medication.
[4]"Minipills" are taken daily continually.
[5]Diethylstilbestrol is taken in a dose of 25 mg, twice daily for 5 days within 72 hours after sexual intercourse.

Many contraceptive preparations are dispensed in convenient calendar-like containers that help the user to count the days. Some obviate the need of counting by incorporating seven blank pills in the package to provide 3 weeks of treatment and I week of no treatment. A pill is taken every day, regardless of when menstruation starts or stops. Iron is included in the "blank" pills in some preparations.

The "minipills" (for example MICRONOR and NOR-QD, containing 0.35 mg of norethindrone, and OVRETTE, containing 75 $\mu$g of norgestrel) are taken daily continually. Since they are less effective and pregnancy is possible during their administration, patients should discontinue the "minipill" if they have amenorrhea for more than 45 to 60 days, and they should be examined for pregnancy. Likewise, if patients have missed one or more pills and have amenorrhea for more than 45 days, they should be similarly evaluated.

Preparations and Dosage of Androgens.

Some parenteral and oral formulations of androgens available for clinical use are summarized in Table 2. Androgen therapy has been used primarily for the development and/or maintenance of secondary sex characteristics. Androgens have been administered through intramuscular preparations but may also be administered orally. Androgens of the present invention include, but are not limited to those listed in Table 2 that may be adapted for use in the described compositions.

TABLE 2

| Non-Proprietary Name | Example of a Trade Name | Dosage Forms and Usual Dosage |
|---|---|---|
| Testosterone | Testoject-50 ™ | Aqueous suspension for intramuscular use: 10 to 50 mg three times weekly |
| Testosterone Propionate | Testex ™ | Oily solution for intramuscular use: 10 to 25 mg two or three times weekly |
| Testosterone Enanthate | Delatestyl | Oily solution for intramuscular use: 50 to 400 mg every 2 to 4 weeks |
| Testosterone Cypionate | Depo-Testosterone | Oily solution for intramuscular use: 50 to 400 mg every 2 to 4 weeks |
| Nandrolone Decanoate | Deca-Durabolin | Oily solution for intramuscular use: 50 to 100 mg every 3 to 4 weeks |
| Nandrolone Phenpropionate | Durabolin | Oily solution for intramuscular use: 50 to 100 mg weekly for breast carcinoma |
| Danazol | Danocrine | Capsules: 200 to 800 mg daily |
| Fluoxymesterone | Halotestin | Tablets: 2.5 to 20 mg daily |
| Methandrostenolone | Dianabol | Tablets: 2.5 to 5 mg daily for osteoporosis |
| Methyltestosterone | Metandren, Oreton Methyl | Tablets and Capsules: 10 to 50 mg daily. Buccal Tablets: 5 to 25 mg daily |
| Oxandrolone | Anavar | Tablets: 2.5 to 20 mg daily |
| Oxymetholone | Anadrol-50 | Tablets: 1 to 5 mg/kg daily for anemia |
| Stanozolol | Winstrol | Tablets: 6 mg daily |
| Testolactone | Teslac | Tablets: 250 mg four times daily for breast carcinoma |

Androgenic Effects on Bone

Without being limited to any particular theory, it is contemplated that the mechanism of oral contraceptive use leading to lower peak bone mass in young women is based on the following considerations. The prime steroid produced by the ovary is androstenedione (A) from which testosterone (T) and estradiol ($E_2$) are derived peripherally. A significant proportion of circulating androgens appear to be derived from the ovary since serum T and A decrease (50%) after oophorectomy (Adashi, 1994; Hughes, et al, 1991).

a) In Vitro Cellular Evidence

Androgen receptors have been identified in osteoblast-like cells (Colvard, et al, 1989; Wiren, et al, 1995) and may modulate calcium channels in bone cells (Takeuchi and Guggino, 1995). In addition, androgens stimulate osteoblast differentiation and proliferation (Kasperk, et al, 1990).

b) Evidence of Androgenic Effects on Bone in Animal Models

Androgens are believed to play a role in building and maintaining bone in the female as well as in the male. The anti-androgen drug, flutamide, inhibits responses to androgens from both the gonads and the adrenals. Osteopenia was induced in intact female rats given flutamide (15 mg/kg body weight orally daily). Bone turnover in female rats with intact ovaries was affected as measured by skeletal $^{45}Ca$ changes suggesting that flutamide-mediated androgen deficiency bone thinning was caused principally by reduced bone formation (Goulding and Gold, 1993). These findings were recently reproduced in intact female rats that were given a pure non-steroidal anti-androgen (Casodex®) daily for 3 weeks. The metaphyseal bone volume and longitudinal bone growth were similar to vehicle-treated intact females. However, dynamic histophometry showed that bon e formation rate was significantly reduced in th e Casodex®-treated rats (Flanagan, et al., 1995).

Direct bone effects by androgens occurred when androstenedione was given to ovariectomized rats and prevented the ovariectomy-induced osteopenia via decreasing bone turnover (Lea, et al. 1995). In older ovariectomized rats, dihydrotestosterone (DHT) was tested because DHT, like testosterone, binds to androgen receptors, but unlike testosterone, DHT cannot be aromatized to estrogen. Both DHT and estradiol provided protection against ovariectomy-induced osteopenia in older ovariectomized rats (Vanin, et al., 1995).

Intramuscular administration of the steroidal anti-androgen cyproterone acetate in white-tailed deer immediately after velvet shedding induced: (a) dramatic reduction of testosterone levels in plasma, (b) premature casting in bucks with fully mineralized antlers and (c) renewal of bone rebuilding activity in incompletely mineralized antlers which resulted in blockage of casting (Bubenik, et al., 1987).

Hormone manipulations in female monkeys affect their body composition and bone mineral status (Jayo, et al., 1989). After one year of hormone treatment via Silastic implants, intact placebo monkeys had lower bone mass of the lumbar spine and whole skeleton than intact monkeys receiving (A+Estrone [$E_1$]) or monkeys receiving testosterone, Testosterone-treated monkeys increased in body weight significantly compared to the other two groups, but both androgen-treated groups significantly increased tibial bone strength and cortical density (Kasra and Grynpas, 1995).

c) Evidence of Androgenic Effects on Bone in Women

Direct evidence for the need of adequate androgenic stimulus in female bone status is shown by a case of a woman with androgen insensitivity that was recently described in Spain. The 17-year-old had poor bone density and elevated levels of androgens. Physicians treated th e young woman with estrogens, but her lack of response to estrogen therapy suggested the importance of an androgenic stimulus even after puberty (Munoz-Torres, et al., 1995). Daniel, et al. (1992) studied the effects of cigarette smoking in young women (25 smokers, 27 nonsmokers) aged 20–35 years. Bone mineral density was not different between groups, but for bo th groups SHBG and free androgen index (T/SHBG) made significant ($p<0.05$) contributions to the variance in bone density.

Adolescent black women have greater bone mass and higher levels of serum testosterone than adolescent white women (Wright, et al., 1995). In a study of elderly black women, bone mass was greater compared with elderly white women. In this elderly group, body mass index ($kg/m^2$) and $E_1$, but not androgens were related to bone mass. Within each race, bone mass increased linearly with increasing concentrations of serum $E_1$ (Cauley, et al, 1994). Furthermore, the levels of free testosterone(fT), but not total T, in older white women relate to the bone density of the spine, hip, and wrist (Greendale, et al., 1995). Thus, de pending on age, the levels of the biologically active if may correlate better with bone mass.

In an earlier study, trabecular bone density correlated significantly only with serum A in women ranging in age from 21 to 48 years (Buchanan, et al., 19 88). Among women with normal serum androgen levels, cortical bone density correlated with serum total T and biologically active fT. It is contemplated that this increased cortical mass should help prevent fractures later in life. Endogenous androgens have an anabolic effect on bone density and trabecular density (spine) was significantly increased in the women with androgen excess (Buchanan, el al., 1988). A correlation was found between sex hormone-binding globulin (SHBG), dihydroepiandrosterone sulfate (DHEAS), androgens, and bone mass in premenopausal women (Johnston, et al., 1993). Free testosterone was the androgen most consistently correlated with bone mass at all measured sites, Therefore, it seems clear that androgens are related to bone mass in premenopausal women.

d) Evidence of Oral Contraceptive Effects on Bone of Premenopausal Monkeys and Women In order to determine the effect of oral contraceptive therapy on bone density and serum markers of bone metabolism, a prospective, longitudinal study of young adult female cynomolgus monkeys was undertaken by the present inventors. Two hundred and seven intact monkeys were divided into two groups, and fed an atherogenic diet containing either no drug (Control) or a triphasic oral contraceptive regimen (Triphasil®).

Pre-treatment and periodic post-treatment measurements of bone density and serum bone biomarkers were performed. No significant differences in pre-treatment variables were observed. Both groups of animals gained bone mineral density (BMD) during the study, indicating that they had not yet reached their peak bone mass. Triphasil®-treated animals gained less lumbar spine bone mineral over the course of the study than control animals, resulting in a lumbar spinal bone mineral density that became significantly different from controls by 20 months. Repeated measures analysis of longitudinal data demonstrated that whole body bone mineral content (BMC) as well as spinal BMC and density were significantly lower in Triphasil®-treated animals compared to untreated intact controls at 10 and 20 months of treatment.

Serum alkaline phosphatase (ALP) levels were markedly reduced in the Triphasil® group, while serum acid phosphatase (ACP) and calcium were reduced to a lesser extent. The results suggest that triphasic oral contraceptive treatment of young adult female monkeys that have not reached peak bone mass inhibits net bone accretion by reducing the rate of bone turnover, an effect which may result in a lower peak bone mass in these animals.

One mechanism to account for these findings is that the balance of bone resorption and bone formation has been altered such that formation is less than resorption. Indeed, oral contraceptive treatment caused a 40% reduction in a marker of bone formation (serum ALP) while causing much smaller changes in resorption markers (10–15% reduction in ACP and only minimal effects on TRAP). Thus, oral contraceptive therapy may reduce bone formation more than bone resorption, such that net bone accretion in these young animals is lessened compared to untreated cycling females.

An additional explanation relates to the idea that there is an optimum window for bone turnover rate above or below which bone will not be sufficiently maintained. Ovariectomy of cynomolgus monkeys results in an elevated bone turnover rate. Like women, treatment of ovariectomized animals with estrogen replacement therapy either with or without medroxyprogesterone acetate results in decreased markers of bone resorption and formation along with increased spinal BMC and BMD compared to untreated controls.

The inventors' oral contraceptive study suggests that decreases in bone turnover in young monkeys before peak bone mass also parallels reductions in bone mineral accretion under different circumstances. Perimenopausal and postmenopausal women may experience bone loss which coincides with an increased bone turnover rate, and estrogen replacement therapy can inhibit this bone loss by reducing bone turnover rate.

In perimenopausal women receiving oral contraceptives, although serum osteocalcin (bone gla protein [BGP]) did not change, urinary excretion of hydroxyproline decreased and paralleled a significant ($p<0.001$) increase in vertebral BMD (Gambacciani, et al., 1994). However, in healthy premenopausal adolescent women and animals, reductions in bone turnover rate may be accompanied by a reduced net bone mineral accretion compared to the normal state, leading ultimately to the achievement of lower peak bone mass.

In a one-year prospective study, the effects of an oral contraceptive containing 20 µg ethinyl estradiol plus 0.1 50 mg desogestrel on bone metabolism were studied in 19 women aged 20 to 30 years. Bone density showed a slight but not significant increase at the end of the trial. Both urinary hydroxyproline-to-creatinine ratio and serum ALP levels showed a significant decrease. The results suggest that bone resorption was reduced, although bone density in the distal radius was not significantly increased in young women using oral contraceptives (Mais, et aL, 1993).

The mean age of the animals at the initiation of the study described in Example 1, below, was estimated through dentition to be 6 years. This is about the time of growth plate closure in this species, but before the attainment of peak bone mass at 9 years (Jayo, et al., 1994). Although women are sexually mature in their early teens, skeletal maturity as reflected by peak bone mass is not reached until about 30 years of age (Recker, et al., 1992). In terms of skeletal maturation, these monkeys may correspond to women between 15 and 30 years of age. Thus, the results may be indicative of oral contraceptive effects on nearly mature skeletons, not in situations where peak bone mass has already been attained. However, the relationship between depression of bone turnover and bone mineral accretion does not appear to be solely due to the fact that the animals are still growing, because trunk length measures did not change significantly between treatment groups.

Pharmacological Compositions

It is understood that the pills formulated for oral administration, including contraceptive pills or even pills, capsules or tablets for use in a hormone replacement regimen may contain ingredients to serve as fillers, binders and for color coding purposes. These ingredients are in common use in present oral contraceptive formulations and may include, but are not limited to, lactose, corn starch, calcium phosphate, povidone, magnesium stearate, stearic acid, colloidal silicon dioxide, hydroxypropyl methylcellulose, polyethylene glycol and one or more of the following dyes: FD&C Blue No. 1 Lake, FD&C Blue No.2 Aluminum Lake, D&C Green No. 5, D&C Yellow No. 10, FD&C Yellow No. 6 or FD&C Red No. 3. Of course these are only exemplary fillers and dyes, those of skill in the art will recognize that other inactive ingredients may be used in the preparation of the formulations of the present invention.

Hormonal preparations as described herein may be prepared for oral administration, and would also include, injectable solutions or suspensions for intramuscular or subcutaneous implantation including long acting injections, and suppositories and topical ointments for vaginal and dermal applications such as skin patches. Solutions of hormonal compounds, analogs, or derivatives can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the hormonal compositions can be brought about by the use in the compositions of agents delaying absorption, for example, aluminum monostearate and gelatin.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the hormonal ingredients, its use in the therapeutic or contraceptive compositions is contemplated.

Androgenic side effects may be experienced at the higher doses. Early side effects that are easily recognized and detected by the patient and physician include acne and hirsutism, both of which imply that dose reduction should be considered. These symptoms are readily reversible if detected early. Advanced hirsutism, voice changes, changes in muscle mass etc. are more advanced androgen excess side effects that are avoidable by response to early detection and adjustment of dosages accordingly. In order to minimize side effects it is suggested that a minimal effective dose for beneficial action on bone mass accrual is in the range of 1.25 mg/day. However it is understood that individual cases may require a greater or lesser dose as deemed necessary by the practitioner.

The hormonal compounds or active ingredients to be used in the compositions and methods described herein may include any of the hormonally active compounds known in the art. The amount of hormonal activity is measurable so that various estrogens may be substituted for ethinyl estradiol, for example, or various progestins substituted for levonorgestrel, or various androgens for methyltestosterone, while achieving the desired levels of hormone activity. The calculation of equivalents of hormononal activity is within the skill in the art, and all such equivalent substitutions for specifically described formulations are also intended to fall within the scope of the present disclosure.

Estrogenic preparations would include natural and synthetic estrogens and would include, but not be limited to diethylstilbestrol, diethylstilbestrol diphosphate hexestrol, methallenestril, promethestrol dipropionate, estradiol, and various ester s thereof (benzoate, cypionate, enanthate, propionate, undecylate, valerate), 17β estradiol, 11-nitrato estradiol, 7-α-methyl-11-nitrato-estradiol, polyestradiol phosphate, estrone and sulfate esters thereof, ethinyl estradiol, mestranol, conjugated estrogens, piperazine estrone sulfate, quinestranol, and esterified estrogens. In terms of activity, some approximately equivalent dosages include: estradiol, 50 µg; mestranol, 80 µg; diethylstilbestrol, 1 mg; conjugated estrogens, 5 mg (For examples, see *Goodman and Gilman's The Pharmacological Basis of Therapeutics*, Chapter 61, MacMillan Publishing Co., Inc. New York, Sixth Edition, 1980).

Various progestins may also be used in the hormonal preparations described herein. Examples would include, but are not limited to levonorgestrel, progesterone, 17-hydroxyprogesterone, desogestrel, 3-keto-desogestrel, ethisterone, medroxyprogesterone acetate , hydroxyprogesterone caproate, norethindrone, norethindrone acetate, norethynodrel, nomegesterol, ethynodiol diacetate, dihydroprogesterone, gestodene, Δ-15-levonorgestrel, nesterone, 17-deacetyl norgestimate, norgestimate, dimethisterone, medroxyprogesterone acetate, ethinylestrenol, megestrol acetate, and norgestrel. Androgens that may be useful in the practice of the claimed invention include, but are not limited to testosterone, testosterone propionate, testosterone enanthate, testosterone cypionate, methyltestosterone, fluoxymesterone, danazol, calusterone, dromostanolone propionate, ethylestrenol, methandriol, methandrostenolone, nandrolone decanoate, nandrolone phenpropionate, oxandrolone, oxymetholone, stanozolol, and testolactone.

Any of the oral tablet formulations presented herein for sequential administration may be supplied in a dispenser designed for a one month supply. A typical dispenser would provide for 28 pills to be taken one a day in a determined order. Exemplary dispensers are those described in U.S. Pat. No. 4,165,709, U.S. Pat. No. 4,807,757, U.S. Pat. No. 3,678,884 or U.S. Pat. No. 3,651,927 (each incorporated herein by reference). It is understood that the dispenser or dispensing means, in and of itself, does not constitute the present invention, and any dispenser means that separates the pills into individual packages and provides a means to dispense the pills one at a time in a particular order so that the user would know which pill to take on any particular day would be acceptable. One or more monthly dispensers may also be contained in a box, such as a cardboard box, for example, that also may contain product information and or instructions for use. The dispensers may also be contained in a decorative type of box that is not immediately identifiable as a birth control pill dispenser.

In those embodiments in which hormone replacement (HRT), or even contraception is desired, the disclosed compositions may be formulated to be administered by use of a skin patch, or transdermal delivery system. The administration of the hormonal compositions described herein transdermally may be accomplished by any of a number of systems known in the art. Examples of systems that may be adapted for use with the compositions described herein include those systems of transdermal estrogens and/or progestin administration described in U.S. Pat. No. 4,816, 252; U.S. Pat. No. 5,122,382; U.S. Pat. No. 5,198,223; U.S. Pat. No. 5,023,084; U.S. Pat. No. 4,906,169; U.S. Pat. No. 5,145,682; U.S. Pat. No. 4,624,665; U.S. Pat. No. 4,687,481; U.S. Pat. No. 4,834,978; and U.S. Pat. No. 4,810,499 (all incorporated herein by reference. In addition, testosterones have also been administered by transdermal means, including non-scrotal transdermal patches (Yu et al., 1997; Meikle et al., 1992; both incorporated herein by reference).

These methods typically include an adhesive matrix or drug reservoir system and may include a skin permeation enhancement agent such as ethanol, polyethylene glycol 200 dilaurate, isopropyl myristate, glycerol trioleate, linolenic acid saturated ethanol, glycerol monooleate, glycerol monolaurate, n-decyl alcohol, capric acid, and certain saturated and unsaturated fatty acids, and their esters, alcohols, monoglycerides, acetate, diethanolamides and N,N-dimethylamides (See for examples, U.S. Pat. No. 4,906, 169).

Sex Hormone Binding Globulin (SHBG)

As discussed elsewhere herein, sex hormone-binding globulin is a serum protein that binds both testosterone and 17β-estradiol, and this binding affects the biological availability of the bound hormones. Oral contraceptives containing a combination of ethinyl estradiol and a progestin have been shown to cause an increase in SHBG, up to 200–240% (Wiegratz et al., 1995). The level of this protein in the blood affects the amount of sex hormones that are available for binding to various receptors that mediate biological activity. In hyperandrogenic women treated with oral contraceptives, estradiol (E2) levels significantly decrease. Thus, estrogen and progestin combination contraceptives, or hormone replacement regimens, cause an increase in SHBG, and higher levels of estrogens have to be administered in order to reach the desired levels of free estrogens in the blood.

Although treatment of post-menopausal women with estrogen alone increased SHBG levels by a factor of approximately 2.8, the combination of estrogen and androgen resulted in a decrease in SHBG to about 60% of the baseline level (Raisz et al., 1996). These data indicate that the addition of an androgen to an oral contraceptive or HRT regimen has two possible mechanisms of increasing the free estrogen that is available to the tissues, by first, competing with the estradiol for binding to SHBG, and second, by causing a decreased secretion of this protein by the liver. In this way, the addition of an androgen allows a much lower level of estrogen to be administered in order to reach the same level of free estradiol in the blood. It is an aspect of the present invention that one may balance the androgen/estrogen/progesterone levels in a pharmaceutical composition in order to achieve an optimal free estrogen level at the lowest concentration of estrogen in the composition by manipulating the androgen level in that composition. It is contemplated by the inventors that a practitioner may be provided a range of various estrogen/androgen/progesterone combinations in order to find the optimal level for a particular patient.

Methodology for Animal Studies

Female cynomolgus monkeys provide a good animal model for examination of hormone effects on bone metabolism. Monkeys have menstrual cycles similar in length and hormonal variations across the cycle to those of women (Mahoney, 1970). In addition, ovariectomized macaques undergo bone changes that respond to estrogen replacement therapy in ways similar to those observed in postmenopausal women (Jerome, et al., 1994). Throughout the trial, bone density, serum and urinary markers of bone turnover, serum sex hormones, plasma lipids, body weight and weight distribution, blood pressure, and bone architecture and morphology were measured. At the end of the trial, all the monkeys were necropsied and the groups compared for bone parameters and coronary artery atherosclerosis (CAA) extent. A prospective trial of this kind cannot be done in human beings because of its invasive nature, expense, and complications from uncontrolled variables.

For the trial, female macaques were divided into 3 groups:

Group 1=Intact, untreated CONTROL

Group 2=Oral contraceptive-treated with Triphasil® p.o., OC

Triphasil®(women's doses): days 1–7, nohormone; days 8–13, 0.03 mg ethinyl estradiol and 0.05 mg levonorgestrel; days 14–18, 0.04 mg ethinyl estradiol and 0.075 mg levonorgestrel; days 19–28, 0.03 mg ethinyl estradiol and 0.125 mg levonorgestrel.

Group 3 Oral contraceptive-treated with Triphasil® plus triphasic methyltestosterone (MT) (Steraloids, Inc., Wilton, N.H.).

Triphasil®+MT (womens doses): days 1–7, no hormone days 8–13, 0.03 mg ethinyl estradiol, 0.05 mg levonorgestrel and 0.40 mg of MT; days 14–18, 0.04 mg ethinyl estradiol, 0.075 mg levonorgestrel, and 0.60 mg of MT; days 19–28, 0.03 mg ethinyl estradiol, 0.125 mg levonorgestrel and 0.40 mg of MT.

Animal Acquisition and Initial Data

One hundred young adult (6 to 8 years old) female cynomolgus monkeys were purchased and imported from Jakarta, Indonesia. The animals were quarantined, as required by law, during which time the experimental diet was given. During the one month baseline period, in vivo bone densitometry and radiography were used to detect bone abnormalities. Animals with skeletal abnormalities or unclosed epiphyses were replaced. Based on anthropometry (body weight and trunk length), bone densitometry, serum chemistry, and plasma lipid results, the monkeys were assigned to three matched groups (as described above). Group equivalence was verified using baseline data. Twenty-four months after treatment, all animals were necropsied to compare study groups for bone structural and strength changes, and CAA.

Iliac bone biopsies for histomorphometric analysis were collected after fluorochrome labeling at baseline and after 12 months of treatment. Blood and urine were collected at 0, 1, 3, 6, 12, 18, and 24 months. Serum and urine biomarkers of bone turnover were measured at all time points. Lumbar spine, hip and whole monkey were measured at 0, 6, 12, and 24 months. Blood lipids measured at 0, 6, 12, 18, and 24 months and LDL molecular weight determinations were performed at month 12. Body measurements (body weight, trunk length, etc.) were taken every six months (at DEXA scan times).

Statistical power calculations (Dupont and Plummer, 1990) were done to determine minimum sample size to detect anticipated differences in means between any two groups. Estimates of variability in bone mineral density (BMD), bone structure evaluated by histomorphometry (Bone volume/total volume % [CnBV%]), serum markers of bone metabolism (alkaline phosphatase, ALP), and CAA intimal areas were calculated from current studies. Table 3 below, lists the adjusted group size (n), detectable difference, power, and two-sided level of significance for primary endpoints.

TABLE 3

Primary Endpoint Data

| Variable | Detectable Difference | Group (n) | Power ($\beta$) | 2-sided ($\alpha$) |
| --- | --- | --- | --- | --- |
| BMD | 4% | 30 | 0.80 | 0.05 |
| CnBV % | 33% | 19 | 0.80 | 0.05 |
| ALP | 23% | 24 | 0.80 | 0.05 |
| CAA | 70% | 30 | 0.75 | 0.05 |

Allowing for a 5% annual mortality rate (based on a present study and after 24 months of treatment; 67 alive from 75 original monkeys), 100 monkeys were randomized into three treatment groups to obtain 90 evaluable animals after two years of treatment. The inventors targeted detectable differences that appear to be clinically relevant, biologically plausible based on endpoints in studies cited above in Table 3, and reasonable based on the inventors findings in a recent thiazide study (Jayo et al., 1995).

Maintenance and Diet Composition

The monkeys were housed in groups of 4 or 5 monkeys in indoor pens (2.0×3.2×2.5 m) which allow unrestricted mobility and social interaction. Water was provided ad libitum by automatic watering devices. Monkeys were fed a moderately atherogenic semi-purified diet. The diet contained 43% of calories from fat and 0.30 mg of cholesterol/Cal. This diet is generally expected to induce total plasma cholesterol concentrations of about 200–400 mg/dl. The diet contains 2.5 IU of vitamin $D_3$/g of diet with a calcium (Ca) to phosphorus (P) ratio of 1.0 (207 mg Ca and 206 mg P per 100 g diet). The vitamin $D_3$ amount and Ca/P ratio are appropriate for this species. The diet has been used previously at the CMCRC (Jayo, et al., 1995). Guidelines established by institutional Animal Care and Use Committee, state and Federal laws, and standards of the Department of Health and Human Services were followed throughout the study.

Triphasil®(ethinyl estradiol [EE] and levonorgestrel [LNG]) were added to this diet composition for Group 2, and Triphasil®plus MT were added to this diet for Group 3. The appropriate drug doses were added to the diet and fed on the prescribed days of the month as described above. The Control group (Group 1) were fed the basic diet without added hormones through the 28-day cycle.

Screening and Sampling

Immediately following the quarantine period, the monkeys entered a 30-day baseline period. During this month, blood and urine were collected for analysis of markers of bone turnover, plasma lipids, and hormone determinations. Animals were sedated ketamine hydrochloride, 15 mg/kg i.m.) for blood and urine collection. Normal ovarian function of the monkeys was determined by following menstrual cycles during quarantine, and by vaginal swabs thereafter. Radiographs were taken for vertebral size, deformity score and pathologic screening. BMC and BMD were measured by DEXA. Body measurements, including BW, trunk length, skinfolds, and trunk and appendicular circumferences were measured. After these determinations, the animals were assigned into three study groups with comparable bone mineral status, anthropometric measurements, serum bone biomarkers, and lipid profiles.

Treatments

Control intact monkeys received no medication mixed in their food. Group 2 animals consisted of intact monkeys given Triphasil®(Wyeth-Ayerst, a triphasic oral contraceptive) for 24 months. Group 3 monkeys were intact given Triphasil®+triphasic methyltestosterone for 24 months. An oral delivery system was selected because this is the route used by women and because the liver may affect drug metabolism. Animals were monitored closely for clinical signs of disease, and if needed, supplements were given in the diet to all groups. A triphasic methyltestosterone formulation was selected based on the normal rhythmic levels of hormone (testosterone/ethinyl estradiol ratio) observed through the female monkey estrous cycle (Wilson, et al., 1982). The doses of MT selected were to provide for an androgenic stimulus similar to T during the estrous cycle. Higher doses present in drug formulations available for postmenopausal women (Estratest®, Solvay Pharmaceuticals, Marietta, Ga.) may cause unwanted side effects in remenopausal adolescent women (Hickock, et al., 1993; Watts, et al., 1995).

General Health Profile

Upon arrival at the center, an initial physical examination provided information on ach animal's health and conditioning. If needed, hematological and clinical chemistry arameters were measured, including complete blood counts and differentials, total serum protein, albumin, serum glucose, urea, nitrogen, creatinine, calcium and phosphate. Urinalysis and fecal samples were tested as needed. A set of normal reference values for female cynomolgus macaques were established. Complete blood counts were done on an automated cell counter (Coulter Counter $M_4$30, Hialeah, Fla.), and leukocyte differentials were also performed. CBCs, liver function tests, total serum protein levels, and glucose were measured throughout the study period.

Body Measurements

Body weight (kg) and trunk length (TL, cm) from suprasternal notch to pubic symphysis were used to calculate body mass index (BMI=BW/[TL/100]$^2$). Thickness (mm) of triceps, subscapular, suprailiac, abdominal, mid-thigh, midscapular, and chest skinfolds were measured. Also, circumference (cm) of waist, hip, thigh, and upper arm were measured (Shively, et al., 1987).

Bone Densitometry

Measurements of bone mineral content and density of lumbar vertebrae (L2-L4), whole monkey, and hip were done in vivo under intramuscular ketamine hydrochloride (15 mg/kg i.m.) and acepromazine maleate (0.15 mg/kg i.m.) anesthesia using procedures previously described (Jayo, et al., 1991). Bone density provides a basis for group assignment and permits comparison of results with similar data from human clinical trials. DEXA scans were taken at baseline and at 6, 12, 18, and 24 months.

Serum and Urine Bone Biomarkers

It is difficult to obtain true and multiple dynamic measurements of bone turnover, especially of resorption, by histomorphometry. Serum and urine biomarkers provide the only economical and practical way to measure formation and resorption without invasive surgery. Serum and urine bone biomarkers were assayed at baseline and at 1, 3, 6, 12, 18, and 24 months. Serum total ALP (bone formation), ACP and tartrate-resistant ACP (TRAP, bone resorption), calcium, and phosphorus were measured using a Cobas Fara Chemistry Analyzer (Roche Diagnostics, Nutley, N.J.) (Carlson, et al., 1992; Jayo et al., 1995; Jerome, et al., 1994). Serum BGP (bone turnover) assays were performed using an established radioimmunoassay. Bone resorption was measured using FDA-approved N-telopeptide collagen excretion markers (Osteomark®, Ostex, Seattle, Wash.). Type I collagen cross-linked N-telopeptides in postmenopausal women are reduced to levels seen in premenopausal women by six weeks of estrogen replacement therapy (Hanson, et al., 1992).

Hormonal Assays

Plasma concentrations of testosterone, free testosterone, methyltestosterone, estrone, estradiol, ethinyl estradiol, sex hormone-binding globulin, and androstenedione were measured by established procedures at the Yerkes Regional Primate Research Center's assay laboratory. MT was measured to test efficacy of delivery system and conversion (if any) to T.

Plasma Lipids

Total plasma cholesterol, triglyceride, and HDL cholesterol analyses (Jayo et al., 1994) were performed by enzymatic techniques using a Cobas Fara Chemistry Analyzer (Roche Diagnostics, Nutley, N.J.). LDL molecular weight and fractionation was also measured.

Blood Pressure Measurements and Electrocardiograms

Blood pressure was measured while the animals were sedated. The animals were laid on their right side, and the right arm was extended in a cephalad direction until the upper arm was approximately perpendicular to the vertical axis of the body. The upper arm circumference was measured midway between the shoulder and the elbow, and an appropriate size cuff was used. Three measurements of systolic blood pressure, diastolic blood pressure, and heart rate were taken (Castro, et al., 1981). The average of these measurements was recorded. Blood pressure was measured with a Dinamap Portable Adult/Pediatric and Neonatal Vital signs Monitor (Model 8100) which uses an oscillometric technique to measure systolic, diastolic, and mean arterial pressures and heart rates non-invasively. This device computes pressures and rates, eliminating subjective interpretation (Corbett, et al., 1981). A Medica Systems (Greendale, N.Y.) Cardiomatic electrocardiograph (Model MSC20001) was used for cardiologic evaluations. Electrocardiograms were taken with the animal placed in dorsal recumbency, and the standard leads (I, II, III, AVR, AVL, AVF) and three chest leads (V-1, V-4, V-6) were recorded.

Bone Collection and Processing for Histomorphometry

Fluorochrome labeling:

Bone histomorphometry requires prior in vivo administration of bone-seeking fluorochrome labels. Monkeys were given sterile intravenous injections on day 1, followed by 14 days of rest and a second labeling injection given on day 21. Seven to 10 days later, a biopsy or necropsy sample was taken. One of the following bone-seeking fluorochromes was used in all monkeys at each of the three bone collection time points: calcein (10 mg/kg), xylenol orange (90 mg/kg), or demeclocycline hydrochloride (20 mg/kg) of course these are only example of fluorochromes and those of skill in the art may employ other fluorochromes.

This type of application allows for dynamic parameters to be measured (Jerome, et al., 1994, Carlson, et al., 1992). Some differences in measured bone formation rates may occur at different time points due to differences in incorporation rates of these labels (Goodwin and Jerome, 1987). By giving the same fluorochrome at each time point there is a reduction in the variability for between-group comparisons at a single time point, but the possible variation in label incorporation is taken into account in analysis of change through time. Measurement of the distance between and extent of labels permits calculation of bone formation rates, while the use of different fluorochrome labels permits the recognition of prior bone mineralization activity.

Iliac Biopsy

Two iliac crest biopsies were collected from each animal, one from each side. Based on available data (Table 10), ovariectomized animals have approximately twice the cancellous bone turnover rate of hormone replaced animals, resulting in replacement of 50–100% of iliac crest cancellous bone each year. Histomorphometric analysis of iliac biopsies taken at one-year intervals enables characterization of functional changes in cancellous bone, since most of the bone present had been formed during the one-year interval. Left iliac crest biopsies were collected aseptically at baseline and from the right ileum one year after initiation of treatment. The method developed by the inventors for iliac bone biopsy in monkeys provides cortical and cancellous bone, with adequate bone area and perimeter for analysis- (Goodwin and Jerome, 1987).

Bone Histologic Processing

Histomorphometry

Iliac biopsies and necropsy bone specimens for histomorphometric analysis were fixed in 70% ethanol, processed, embedded in methyl methacrylate/dibutyl phthalate, and sectioned by one or both of the following methods: 1) Sectioned with a LKB Macrotome sledge microtome or a Jung Supercut rotary microtome at 5–10 µm, and mounted unstained or stained with alkaline toluidine blue or modified Von Kossa method; or 2) sectioned at 100–125 µm using an Isomet saw (Buehler, Lake Bluff, Ill.), microradiographed in a Faxitron cabinet (Hewlett-Packard, Rockville, Md.), and/ or stuck to glass slides, polished, and surface stained by von Kossa methodology.

Immunocytochemistry

Selected necropsy specimens were fixed in freshly prepared cold 4% paraformaldehyde to maintain antigenic properties and processed in one or both of the following two methods: 1) embedded in methylmethacrylate, undecalcified or 2) decalcified in 1% EDTA, paraffin embedded, and serially sectioned for immunocytochemical or in situ hybridization studies. The inventors have developed reliable techniques that enable the evaluation of the presence and/or production of bone-related proteins (Tulli, et al., 1992; Carlson, et al., 1993).

Standard Histomorphometry of Multiple Bone Envelopes

The present study uses modification of methods described by Parfitt, et al. (1987a). The measurements and abbreviations used were based on the ASBMR standard nomenclature (Parfitt, et al., 1987b). Structural and dynamic parameters were derived separately for periosteal (Ps), haversian (H), endocortical (Ec), and cancellous (Cn) bone envelopes. Bone volume was also calculated for H+Ec and for all (Tt) envelopes combined. This analysis is primarily of value for analysis of dynamic (functional) changes in bone, enabling assessment of the relative contributions of the cortical-endosteal and cancellous envelopes to bone macro- and microarchitectural changes. Using this method, it is possible to determine the relative contributions of the different envelopes to structural change resulting from experimental manipulation. Additional parameters which may be included in this analysis are measurement of erosion depth and wall thickness to determine bone balance per remodeling cycle and activation frequency (Cohen-Solal, et al., 1991). This analysis is time consuming, and even with the assistance of automated methods, is only feasible on one section per bone.

Automated Histomorphometric Analysis of Multiple Bone Sections

Multiple cross-sections of femur neck, femur diaphysis, lumbar vertebra, and distal radius were cut with an Isomet saw, surface-stained and/or microradiographed, and analyzed using an Apple Power PC with NIH Image Analysis System. Microradiographed or von Kossa-stained sections have sufficiently high contrast that bone and marrow can be readily distinguished by thresholding of gray-scale images obtained with a color camera. The thresholded gray-scale images are converted to binary bit-maps (which may be represented as black and white images), from which measurements can be extracted rapidly.

Necropsies and Tissue Collection

After the 24-month DEXA scan, the animals were further sedated with ketamine hydrochloride (10 mg/kg body weight) for transport to the necropsy laboratory. Sodium pentobarbital (13 mg/kg body weight) was administered intravenously to attain surgical anesthesia. An infusion of Ringer's solution is initiated via an 18 gauge needle inserted into the left ventricle. Euthanasia was effected with a 5 ml (325 mg) intravenous injection of sodium pentobarbital. A 1 cm longitudinal incision made in the abdominal inferior vena cava allowed drainage of blood from the cardiovascular system. The heart and major vessels were dissected out and prepared for perfusion with 10% neutral buffered formalin (NBF) at a pressure of 100 mm/Hg for 1 hour. The heart, aorta and carotid and iliac arteries were carefully dissected free and immersion fixed in 10% NBF until further preparation. The brains, including the intracranial arteries, were removed and immersion fixed in 20% NBF. All major organ systems were examined grossly. Reproductive, endocrine, cardiovascular, and other soft tissues were collected, fixed in 4% paraformaldehyde and/or snap frozen with liquid nitrogen, and carefully evaluated for changes due to treatment.

After the soft tissues were removed from the carcass, both femoral heads are ex vivo scanned by DEXA at a high resolution to describe regional differences in BMC, including the femoral neck, Ward's triangle, and mid-diaphysis (cortical bone). Both humeri, the right femur, and the lumbar 3 & 4 vertebrae as a pair were wrapped in wet (Ringer's or saline) gauze, identified with a tag, and placed in properly labeled Ziploc® bags to be frozen at −20° C and used as needed for further study.

The left radius and lumbar 2 and 5, and thoracic vertebrae 6 through 9 were fixed in 70% ethanol for histomorphometric analysis. The left femur was placed in 10% NBF for DEXA scan and then transferred to 70% ethanol. Both knees were fixed in 10% NBF and later in 70% ethanol for arthritis evaluation of articular cartilage and subchondral bone. Sternebrae and thoracic vertebra 13 were sectioned longitudinally (I to 3 mm thick) with the Isomet saw (after removal of dorsal arches and transverse processes), and fixed in cold 4% paraformaldehyde. After 24 hours, these sections were transferred to 40% ethanol. The slabs were processed for immunocytochemistry (Tulli, et al., 1992) and in situ hybridization.

Biomechanical Testing

Frozen bones were submitted for biomechanical fracture tests and bone strength analyses. Mechanical testing includes shear tests on the femoral necks, three-point bending of humerus mid-diaphysis, and fatigue testing on vertebrae.

Coronary Artery Atherosclerosis Evaluation

To study the extent and severity of coronary artery atherosclerosis, 15 blocks (each 3 mm in length) cut perpendicularly to the long axis of the arteries were taken. Five of these were serial blocks from the left circumflex, five from the left anterior descending, and five from the right coronary artery. The tissue blocks were dehydrated through increasing concentrations of ethanol and embedded in paraffin. Two sections (5 µm) were cut from each block and stained with either hematoxylin and eosin or Verhoeff-van Gieson's stain and morphometrically evaluated. Verhoeff-van Gieson's stained sections of arteries were projected, using a projection microscope, onto a digitizer plate. Using a hand-held stylus and a computer-assisted digitizer, the component parts of the artery were traced.

Measurements of the intimal area, intima area per unit length of internal elastic lamina, area within the internal elastic lamina, and coronary artery luminal area were taken. Intimal areas were determined by digitizing the area between the internal elastic lamina and the luminal surface of each coronary artery section. An integration method was used for calculations of intimal areas. The area of the intima describes plaque size. To obtain the intimal area per unit length of internal elastic lamina, the length of the internal elastic lamina was divided into the intimal area. This measurement provides information about the average intimal thickness for a given section of coronary artery. The length of the internal elastic lamina (circumference) was used to calculate the area. This measurement characterizes artery size. The area within the external elastic lamina could be measured, but the interpretation of its precise location is less clear than that of the internal elastic lamina. The two measurements were correlated highly, hence internal elastic lamina was used as a measure of size.

Soft Tissue Evaluation

Formalin-fixed, paraffin-embedded, and hematoxylin and eosin stained sections of all other soft tissues were evaluated.

Data Analysis and Interpretation

Statistical Methods

Values obtained by sequential sampling, such as histomorphometry, densitometry, and serum and urine chemistry measurements, were analyzed using repeated measures analysis of variance (ANOVA) or covariance (ANCOVA) or by appropriate nonparametric methods. Where comparisons of any two data points were of interest, appropriate parametric (t-statistics) or nonparametric (Mann-Whitney or Wilcoxon) tests were used. Regression and correlation models (parametric and nonparametric) were used to examine the relationships between variables; for example, the correlation between histomorphometric and absorptiometric measures. Linear and curvilinear regression analyses were used to examine rates of change over time. All parametric analyses presented used the methods of Sokal and Rohlf (1981), and nonparametric analyses used the methods of Seigel (1956).

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention.

EXAMPLE 1

Oral Contraceptive Effects on Bone Metabolism in Primates

Animals

Two hundred and seven female cynomolgus monkeys (*Macaca fascicularis*) were part of a comparative clinical trial designed to determine if the premenopausal use of a contraceptive steroid (Triphasil®) influenced the progression of CAA and osteoporosis after surgical menopause. The average age (estimated by dentition) of the animals was approximately 6 years, and was not significantly different between groups (p>0.40). The 207 animals were randomized to one of two treatment groups of 103 untreated animals (Control) and 104 oral contraceptive (Triphasil®)-treated animals. The data presented here were transformed when necessary to reduce skewness and equalize group variances, and subjected to analysis of variance (ANOVA) or repeated measures analysis of covariance (ANCOVA). All data presented represent the mean±SEM of the untransformed data. Longitudinal bone densitometry data from 0, 10 and 20 months were analyzed by repeated measures ANCOVA. Data from 0 months (baseline) were used to control for pre-treatment variation.

Drug Administration

Female cynomolgus monkeys consume approximately 17% of the calories (dose) of the average woman, or about 306 calories/day. Oral contraceptive dosage was calculated to approximate the human dose based on an estimated caloric intake of 120 calories/kg body weight (or 1800 calories/day for an average adult woman) and given mixed in the diet. Therefore, the Triphasil®-treated monkeys were fed four separate diet formulations (days 1–7, no hormone; days 8–13, 0.03 mg ethinyl estradiol and 0.05 mg levonorgestrel; days 14–18, 0.04 mg ethinyl estradiol and 0.075 mg levonorgestrel; days 19–28, 0.03 mg ethinyl estradiol and 0.125 mg levonorgestrel).

The diets contained 0.55 IU Vitamin $D_3$/calorie (168 IU/day), 1.75 mg calcium/calorie (535 mg/day), and 1.49 mg phosphorus/calorie (456 mg/day) for a calcium/phosphorus ratio of 1.17. This level of calcium intake translates to 3,147 mg calcium/day for a woman consuming 1800 calories/day, which is >3 times the calcium intake (1000 mg/day) recommended for young women (see Kanders, et al., 1988), and is more than twice the recommended calcium intake of 1500 mg/day for postmenopausal women. The dietary vitamin $D_3$ levels correspond to about twice the recommended daily dose in women.

Bone Densitometry

Lumbar spine (L2-L4) bone mineral content (BMCsp, g) and density (BMDsp, g/cm$^2$), and whole body bone mineral content (BMCW, g) were measure d with a Norland XR26 dual-energy X-ray absorptiometer (DEXA; Norland, Ft. Atkinson, Wis.). Two hundred and seven animals were scanned once at time 0 and after 10 months of treatment, of these 188 were also scanned after 20 months of treatment. BMCsp was not significantly different between groups at any time point. BMDsp was not significantly different between groups at time 0, but became significantly lower (p<0.05) in the Triphasil® group at 10 months, and remained significantly lower after 20 months of treatment.)While BMCsp and BMDsp both increased with time, there were significant group X time interactions, indicating that the treatment groups were changing differently over time.

Triphasil® animals had smaller increases in BMCsp and BMDsp over time compared to untreated Controls. BMCw also increased with time in both groups, and there was also a significant group X time interaction. Triphasil® animals gained less BMCw than Controls after 10 months of treatment.

Serum Biomarkers

Serum was collected prior to treatment and at regular 5-month intervals during treatment for assessment of circulating markers of bone metabolism. Sampling was carried out on day 21 of the hormonal regimen. Serum ALP (U/L), ACP (U/L), TRAP (U/L), calcium (Ca$^{2+}$, mg/dl, and inorganic phosphate (Pi, mg/dl) were determined using a Cobas Fara 11 autoanalyzer employing protocols and reagents supplied by Roche Diagnostic Systems, Inc. nutley, N.J.). Serum ALP levels were decreased by about 43% compared to the baseline values in the Triphasil® group, while decreasing only slightly (12%) in the Control group compared to baseline values. During the course of the study, the serum ALP activity in Triphasil®-treated animals was approximately 55–60% of that in the control group. Serum ACP and Ca$^{2+}$ also were significantly lower in the Triphasil® animals, while no significant treatment effect was observed on TRAP, but cyclical effects were seen in the serum Pi levels. Consequently, the Triphasil® group had reduced serum markers of bone resorption (ACP) and bone formation (ALP).

Serum Androgen Levels

Oral contraceptive use causes a time-dependent suppression of serum DHEAS by 20–30% (p<0.01) and A, and a significant decrease in levels of total T by 30–35% (p<0.01) and fT by 60% (p<0.01), while SHBG was increased by 200–240% on days 11 and 21 (p<0.01). The results demonstrate a profound suppression of androgen levels and peripheral androgen metabolism (Wiegratz, et al., 1995; Kuhnz, et al., 1994).

In the monkey study, serum was collected at 10 and 20 months and total T, A, and DHEAS measured. As shown in Table 4, the Triphasil® group had approximately half the serum levels of androgens than the Control group.

TABLE 4

Serum androgen concentrations in premenopausal monkeys (mean ± SEM).

|  | Control | Triphasil ® | p-value |
|---|---|---|---|
| T (ng/ml) | 0.367 ± 0.019 | 0.182 ± 0.009 | 0.0001 |
| A (ng/ml) | 3.96 ± 0.191 | 1.89 ± 0.092 | 0.0001 |
| DHEAS (µg/ml) | 15.43 ± 1.06 | 12.09 ± 0.86 | 0.015 |

Anthropometric and Densitometric Measurements

Anthropometric and densitometric measures (means±sem) for the two treatment groups at the various time points are presented in Table 5. As denoted in Table 5, the number of observations per group decreased over time in the study, as densitometry data was available for 207 animals at the 0 and 10 month time points and 188 animals at the 20 months time point. For this reason, each time point was initially analyzed separately. Body weight, trunk length, BMCw, and BMCs were not significantly different between groups at any time point. BMDs was not significantly different between groups at time 0, but became significantly lower in the Contraceptive group at 10 months, and remained significantly lower after 20 months of treatment.

Since the number of observations decreased by the third time point (20 months), the data were analyzed by a 2×2 analysis of variance for the 0 and 10 month data. In order to examine long term effects, the data were analyzed by 2×3 ANOVA of all three time points or a 2×2 ANCOVA of the 10 and 20 month measurements adjusted for pretreatment measures.

TABLE 5

Analysis of variance for individual time point comparisons of anthropometric and densitometric data for 207 intact female cynomolgus macaques at 0 and 10 months and 188 animals at 20 months taking placebo (CONTROL) or contraceptives (CONTRACEPTIVE) and analyses of variance (ANOVA). Values are means ± s.e.

|  | CONTROL | CONTRACEPTIVE | n | p |
|---|---|---|---|---|
| Body Weight (kg) |  |  |  |  |
| 0 months | 2.80 ± 0.04 | 2.89 ± 0.04 | 207 | 0.15 |
| 10 months | 2.89 ± 0.04 | 2.97 ± 0.04 | 207 | 0.20 |
| 20 months | 2.89 ± 0.04 | 299 ± 004 | 188 | 0.08 |
| Trunk Length (cm) |  |  |  |  |
| 0 months | 26.9 ± 0.01 | 27.0 ± 0.01 | 207 | 0.59 |
| 10 months | 27.0 ± 0.01 | 27.1 ± 0.01 | 207 | 0.42 |
| 20 months | 27.0 ± 0.01 | 27.2 ± 0.01 | 188 | 0.23 |
| BMC-Spine L2-4 (g) |  |  |  |  |
| 0 months | 4.23 ± 0.08 | 4.27 ± 0.07 | 207 | 0.73 |
| 10 months | 4.54 ± 0.08 | 4.46 ± 0.08 | 207 | 0.46 |
| 20 months | 4.63 ± 0.09 | 4.50 ± 0.08 | 188 | 0.30 |
| BMC-Spine L2-4 (g/cm2) |  |  |  |  |
| 0 months | 0.476 ± 0.006 | 0.473 ± 0.005 | 207 | 0.65 |
| 10 months | 0.507 ± 0.006 | 0.490 ± 0.006 | 207 | 0.04 |
| 20 months | 0.515 ± 0.006 | 0.494 ± 0.006 | 188 | 0.02 |
| BMC Whole Body (g) |  |  |  |  |
| 0 months | 111.5 ± 2.1 | 114.1 ± 2.0 | 207 | 0.78 |
| 10 months | 122.3 ± 2.2 | 122.6 ± 2.0 | 207 | 0.91 |
| 20 months | 123.8 ± 2.5 | 122.7 ± 2.0 | 188 | 0.72 |

The results from repeated measures ANOVA at 0 and 10 months for these variables are presented in Table 6. Body weight, which was not different between groups at baseline, increased significantly in both groups with time on diet. No group or time effects were found for trunk length over the first 10 months. While spinal (L2-4) BMC and BMD both increased with time, there were significant group x time interactions, indicating that the treatment groups were changing differently over time. Oral contraceptive treated animals had smaller increases in spinal BMC and BMD over time compared to untreated controls. Whole body BMC also increased with time in both groups, and there was also a significant group x time interaction. Contraceptive-treated animals gained less BMC than controls after 10 months of treatment.

TABLE 6

Repeated measures analysis of variance for anthropometric and densitometric measurements of 207 intact female cynomolgus macaques taking placebo (CONTROL) or contraceptives (CONTRACEPTIVES) at 0 months (baseline) and after 10 months of treatment.

|  |  | p |
| --- | --- | --- |
| BODY WEIGHT (kg) | group | 0.168 |
|  | time | 0.000 |
|  | group x time interaction | 0.792 |
| TRUNK LENGTH (cm) | group | 0.493 |
|  | time | 0.113 |
|  | group x time interaction | 0.402 |
| BMC-SPINE L2-4 (g) | group | 0.831 |
|  | time | 0.000 |
|  | group x time interaction | 0.001 |
| BMD-SPINE L2-4 (g/cm$^2$) | group | 0.201 |
|  | time | 0.000 |
|  | group x time interaction | 0.000 |
| BMC-WHOLE BODY (g) | group | 0.621 |
|  | time | 0.000 |
|  | group x time interaction | 0.025 |

Longitudinal anthropometric and bone densitometry data from 0, 10 and 20 months was analyzed by repeated measures ANCOVA. Data from 0 months (baseline) was used to control for pretreatment variation. Individual means and standard deviations of the data from animals receiving evaluations at all three time points are presented, along with ANCOVA statistics and adjusted cell means (Tables 7 and 8). Values vary slightly from that presented in Table 5 due to the elimination of incomplete data. Body weight, which significantly increased over the first 10 months, did not change over the second 10 month period and showed no group or group x time interactions (Table 7). Trunk length increased over time as evidenced by a very slight increase in both groups, although no group or group x time interactions were observed.

TABLE 7

Repeated measures analysis of variance[1] and covariance[2] for the complete anthropomorphic data from 0, 10 and 20 month time points (group means ± sem).

| BODY WEIGHT (kg) | CONTROL (n = 91) | CONTRACEPTIVE (n = 97) |
| --- | --- | --- |
| 0 MONTHS | 2.80 ± 0.04 | 2.91 ± 0.04 |
| 10 MONTHS | 2.89 ± 0.04 | 3.00 ± 0.04 |
| 20 MONTHS | 2.89 ± 0.04 | 2.99 ± 0.04 |

[1][NO COVARIATE], group p = 0.06; time p = 0.00; group x time interaction p = 0.98
[2][COVARIATE = BW AT 0 MONTHS], group p = 0.75; time p = 0.59; group x time interaction p = 0.92.

TABLE 7-continued

Repeated measures analysis of variance[1] and covariance[2] for the complete anthropomorphic data from 0, 10 and 20 month time points (group means ± sem).

| TRUNK LENGTH (cm) | CONTROL (n = 91) | CONTRACEPTIVE (n = 97) |
| --- | --- | --- |
| 0 MONTHS | 26.9 ± 0.1 | 27.1 ± 0.1 |
| 10 MONTHS | 26.9 ± 0.1 | 27.2 ± 0.1 |
| 20 MONTHS | 27.0 ± 0.1 | 27.2 ± 0.1 |

[1][NO COVARIATE], group p = 0.26; time p = 0.00; group x time interaction p = 0.40
[2][COVARIATE = TL AT 0 MONTHS), group p = 0.17; time p = 0.01; group x time interaction p = 0.86.

After adjusting for pretreatment (time 0) differences, significant group, time, and group by time effects were observed for lumbar spinal bone mineral content and density (Table 8). Spinal BMC and BMC increased in both groups between 0 and 10 months, with much smaller increases occurring between 10 and 20 months. Contraceptive-treated animals gained bone at a reduced rate compared to controls, resulting in a lower spinal BMC and BMC at 10 and 20 months of treatment. Significant group, time, and group by time interactions were also observed for whole body BMC. Whole body BMC increased significantly in both Control and in Contraceptive-treated animals over the first 10 months, and increased slightly over the next 10 months in the Control group while decreasing slightly in the Contraceptive group.

TABLE 8

Repeated measures analysis of variance and covariance for complete bone densitometry data from 0, 10 and 20 month time points (group means ± sem). Adjusted means for covariate analysis are presented in brackets [].

BMC SPINE (g)

| | CONTROL | CONTRACEPTIVE |
| --- | --- | --- |
| 0 MONTHS | 4.22 ± 0.08 | 4.29 ± 0.08 |
| 10 MONTHS | 4.52 ± 0.08 [4.56] | 4.48 ± 0.08 [4.45] |
| 20 MONTHS | 4.62 ± 0.09 [4.66] | 4.50 ± 0.08 [4.46] |

[1][NO COVARIATE], group p = 0.78; time p = 0.00; group x time interaction p = 0.00
[2][COVARIATE = BMC(SPINE), TRUNK LENGTH AT 0 MONTHS], group p = 0.00; time p = 0.00; group x time p = 0.00.

BMD SPINE (g/cm$^2$)

| | CONTROL | CONTRACEPTIVE |
| --- | --- | --- |
| 0 MONTHS | 0.476 ± 0.006 | 0.473 ± 0.006 |
| 10 MONTHS | 0.506 ± 0.006 [0.505] | 0.491 ± 0.006 [0.491] |
| 20 MONTHS | 0.515 ± 0.006 [0.514] | 0.494 ± 0.006 [0.494] |

[1][NO COVARIATE], group p = 0.12; time p = 0.00; group x time interaction p = 0.00
[2][COVARIATE = BMD(SPINE), BMC(SPINE) AT 0 MONTHS], group p = 0.00; time p = 0.00; group x time p = 0.03

| BMC WHOLE BODY (g) | CONTROL (n = 91) | CONTRACEPTIVE (n = 97) |
| --- | --- | --- |
| 0 MONTHS | 111.4 ± 2.0 | 115.0 ± 2.0 |
| 10 MONTHS | 122.0 ± 2.2 [123.8] | 124.0 ± 2.0 [122.4] |
| 20 MONTHS | 123.8 ± 2.4 [125.5] | 122.7 J ± 2.0 [121.0] |

[1][NO COVARIATE], group p = 0.61; time p = 0.00; group x time interaction p = 0.00
[2][COVARIATE = BMC(WHOLE BODY), BMC(SPINE) AT 0 MONTHS], group p = 0.00; time p = 0.71; group x time p = 0.00

Bone Biomarkers

Serum biomarker analysis results are presented in Table 9. Since the number of observations changed over time, group comparisons were made for each individual time point. Serum alkaline phosphatase levels were decreased by about 43% compared to the pretreatment (time 0) values in the Contraceptive group, while decreasing only slightly (12%) in the control group compared to pretreatment values. During the course of treatment, the serum alkaline phosphatase activity in contraceptive treated animals was approximately 55–60% of that found in the control group. Serum acid phosphatase and calcium were also significantly lower in the Contraceptive group, while no consistent effect was observed on tartrate-resistant acid phosphatase or serum phosphate levels. Thus, the Contraceptive group had reduced serum markers of bone resorption (acid phosphatase) and bone formation (alkaline phosphatase).

TABLE 9

Analysis of variance for individual time point comparisons of serum biomarker data.

|  | CONTROL | CONTRACEPTIVE | n | $p =$ |
|---|---|---|---|---|
| ALKALINE PHOSPHATASE (U/L) | | | | |
| 0 MONTHS | 197.1 ± 6.8 | 180.2 ± 7.2 | 180 | 0.090 |
| 5 MONTHS | 173.5 ± 6.9 | 103.5 ± 5.9 | 113 | 0.000 |
| 10 MONTHS | 172.7 ± 4.9 | 104.7 ± 3.3 | 174 | 0.000 |
| 15 MONTHS | 190.9 ± 9.1 | 104.8 ± 4.4 | 171 | 0.000 |
| 20 MONTHS | 173.4 ± 9.0 | 102.5 ± 6.8 | 60 | 0.000 |
| ACID PHOSPHATASE (U/L) | | | | |
| 0 MONTHS | 8.39 ± 0.21 | 8.47 ± 0.25 | 180 | 0.820 |
| 5 MONTHS | 8.35 ± 0.31 | 7.89 ± 0.32 | 113 | 0.307 |
| 10 MONTHS | 8.90 ± 0.23 | 7.89 ± 0.17 | 174 | 0.006 |
| 15 MONTHS | 9.01 ± 0.22 | 8.11 ± 0.18 | 172 | 0.002 |
| 20 MONTHS | 8.72 ± 0.35 | 7.07 ± 0.35 | 59 | 0.002 |
| TARTRATE RESISTANT ACID PHOSPHATASE (U/L) | | | | |
| 0 MONTHS | 3.70 ± 0.07 | 3.80 ± 0.06 | 178 | 0.280 |
| 5 MONTHS | 4.12 ± 0.10 | 3.68 ± 0.15 | 113 | 0.013 |
| 10 MONTHS | 4.44 ± 0.09 | 4.33 ± 0.09 | 174 | 0.360 |
| 15 MONTHS | 4.14 ± 0.08 | 4.09 ± 0.10 | 172 | 0.700 |
| 20 MONTHS | 4.35 ± 0.19 | 4.09 ± 0.16 | 59 | 0.306 |
| CALCIUM (mg/dl) | | | | |
| 0 MONTHS | 9.23 ± 0.04 | 9.27 ± 0.04 | 180 | 0.470 |
| 5 MONTHS | 9.12 ± 0.05 | 8.90 ± 0.05 | 113 | 0.005 |
| 10 MONTHS | 9.19 ± 0.07 | 8.96 ± 0.05 | 174 | 0.008 |
| 15 MONTHS | 8.98 ± 0.05 | 8.73 ± 0.04 | 172 | 0.000 |
| 20 MONTHS | 9.03 ± 0.07 | 8.85 ± 0.08 | 60 | 0.092 |
| PHOSPHATE (mg/dl) | | | | |
| 0 MONTHS | 3.78 ± 0.11 | 3.51 ± 0.11 | 180 | 0.079 |
| 5 MONTHS | 3.67 ± 0.08 | 3.99 ± 0.10 | 113 | 0.082 |
| 10 MONTHS | 3.74 ± 0.10 | 3.97 ± 0.09 | 174 | 0.097 |
| 15 MONTHS | 3.71 ± 0.08 | 3.46 ± 0.07 | 172 | 0.015 |
| 20 MONTHS | 3.77 ± 0.14 | 4.00 ± 0.15 | 60 | 0.272 |

The biochemical findings described above suggest that oral contraceptive treatment caused an overall reduction in bone turnover in these animals. Reduction of bone turnover rate is usually associated with preservation of bone mineral, since estrogen replacement therapy appears to preserve bone density in ovariectomized monkeys by reductions in the overall turnover rate. In this case, however, oral contraceptive treatment resulted in reduction of biomarkers of bone turnover along with an apparently negative effect on net bone mineral density relative to Control animals.

These data show that prolonged oral contraceptive treatment reduces net bone accretion and may result in a lower peak bone mass in young female monkeys that are still accruing bone.

EXAMPLE 2

Estrogen Effects on Postmenopausal Monkeys:
Bone Histology and Biomechanics

This Example presents the histomorphometric data from studies of postmenopausal monkeys.

Bone Histomorphometry

In untreated ovariectomized women, as in estrogen-deficient ovariectomized monkeys, when bone turnover increases the net effect is bone loss. Previous reports have demonstrated a good correlation between serum markers and histomorphometric data (Jerome, et al., 1994). Studies of the structural changes that occur after ovariectomy in cancellous bone of iliac and lumbar bones of monkeys after 11 months of treatment have been made (Jayo, et al., 1995). Animals were bilaterally ovariectomized and divided into 3 groups: 1) untreated (OVX),2) receiving estrogen replacement therapy (ERT), and 3) receiving ERT plus thiazide diuretics (ERT+TZ). Table 10 provides iliac cancellous bone histomorphometric information.

TABLE 10

Structural Histomorphometry of Iliac Cancellous Bone in OVX, OVX + ERT, and ERT + TZ Cynomolgus Monkeys (Mean ± SEM, adapted from Jayo, et al, 1995).

| Measurement | OVX (n = 10) | ERT (n = 10) | ERT + TZ (n = 10) | p-value |
|---|---|---|---|---|
| Cancellous bone volume (%) | | | | |
| 0 months | 28.87 ± 2.03 | 27.17 ± 2.97 | 25.47 ± 2.19 | NS |
| 11 months | 17.92 ± 1.51 | 25.65 ± 2.63 | 23.62 ± 1.91 | 0.036 |
| Trabecular thickness (um) | | | | |
| 0 months | 130.00 ± 6.27 | 138.05 ± 5.53 | 119.12 7.76 | NS |
| 11 months | 102.12 ± 6.44 | 110.85 ± 7.16 | 101.71 6.29 | NS |
| Trabecular n (/mm) | | | | |
| 0 months | 2.23 ± 0.14 | 1.95 ± 0.18 | 2.14 ± 0.12 | NS |
| 11 months | 1.68 ± 0.14 | 2.23 ± 0.18 | 2.28 ± 0.16 | 0.023 |
| Trabecular separation (um) | | | | |
| 0 months | 334.08 ± 28.83 | 412.61 ± 50.08 | 365.54 ± 35.77 | NS |
| 11 months | 540.43 ± 63.10 | 370.66 ± 51.83 | 355.36 ± 29.24 | 0.026 |

Structural changes in midsagittal sections of vertebral cancellous (lumbar) bone 25 months after ovariectomy in monkeys have been documented (Carlson, et al, 1992; Jerome, et al, 1994). There were significant differences in vertebral cancellous bone volume and trabecular thickness, but not in trabecular number or separation between groups (Table 11).

TABLE 11

Structural and Dynamic Histomorphometry of Vertebral Cancellous Bone in Ovariectomized (OVX), OVX + 17-β Estradiol (ERT), and OVX + 17-β Estradiol + Progesterone-treated (ERT + P) Cynomolgus Monkeys (adapted from Jerome, et al, 1994)

| Measurement | OVX (n = 10) | ERT (n = 10) | ERT + P |
|---|---|---|---|
| Cancellous bone volume (%) | 24.3 ± 1.2 | 24.6 ± 1.3 | 8.6 ± 1.02* |
| Osteoid Surface (OS/BS, um) | 17.5 ± 3.1 | 6.8 ± 0.9† | 11.9 ± 2.2 |
| Mineral Apposition Rate ($\mu$m/day) | 0.65 ± 0.03 | 0.48 ± 0.02† | 0.56 ± 0.03‡ |

*p < 0.05 vs OVX and ERT
†p < 0.05 vs OVX
‡p < 1.0 vs ERT

In summary, serum biomarker and histomorphometric data indicate that bone formation rate is markedly increased after surgical menopause in monkeys and that bone turnover generally remains elevated for at least 2 years. This functional change is accompanied by architectural changes in cancellous bone and trends toward, and consistent with, a loss of structural elements. In order to test the consequences of having a loss in structural elements, the biomechanical force required to cause a fracture in bone of ovariectomized animals was tested.

Bone Biomechanical Testing

Tibiae collected 30 months after surgery from INT and OVX macaques were collected, frozen, and were tested using an Instron materials testing system (Kasra and Grynpas, 1992). The midshaft was loaded in nondestructive 3-point bending tests to determine modulus of elasticity, followed by destructive torsion tests to determine shear modulus and failure shear stress. Mid-shaft cross-sectional area also was measured. Although cross-sectional area was not different between groups, all other parameters were significantly lower in OVX animals compared to INT animals (p<0.05), indicating a postmenopausal weakening of the mechanical properties of the bone and increased fragility (Table 12).

TABLE 12

Mechanical properties of the tibiae of intact (INT) and ovariectomized (OVX) cynmolgus macaques 30 months after surgery (mean ± SD, 2-tailed t-test).

| Test | INT (n = 11) | OVX (n = 11) | p-value |
|---|---|---|---|
| Elastic modulus (MPa) | 9044 ± 400 | 7193 ± 412 | <0.01 |
| Shear modulus (MPa) | 2849 ± 138 | 2215 ± 147 | <0.05 |
| Failure stress (MPa) | 47 ± 2.4 | 35 ± 2.1 | <0.05 |
| Area (mm$^2$) | 37 ± 1.2 | 37 ± 1.5 | NS |

The effects of androgens on the biomechanical properties of bone were evaluated in intact female monkeys (INT), intact monkeys treated with androstenedione plus $E_1$ (ANDRO), and intact monkeys treated with testosterone (TESTO) (Adams, et al, 1995; Kasra and Grynpas, 1995). In this study the TESTO monkeys received supraphysiological levels of T, giving them blood levels of T similar to male monkeys and also a male body composition. Core samples from the femoral head were studied and the results are given in Table 13.

TABLE 13

Mechanical properties of the femoral trabecular bone of INT, ANDRO and TESTO cynomolgus macaques 30 months after treatment (mean ± sd, n = 12 per group). Adapted from Kasra, et al, 1995. Symbols in common are significantly different (p < 0.05).

| Test | INT | ANDRO | TESTO |
|---|---|---|---|
| Elastic modulus (MPa) | 392 ± 70*† | 737 ± 152† | 812 ± 123* |
| Maximum Stress (MPa) | 23.6 ± 4.8* | 23.2 ± 2.6† | 29.8 ± 5.4*† |
| Density (g/cm$^3$) | 1.326 ± 0.09* | 1.389 ± 0.05 | 1.440 ± 0.06* |

The tibia were also biomechanically tested, and the TESTO group had stronger, tougher, and stiffer tibiae (Kasra and Grynpas, 1995).

These bone studies indicate that skeletal changes in surgically postmenopausal acaques are similar to those that occur in postmenopausal women, including increased bon e turnover, decreased bone mass, altered cancellous bone microarchitecture, and compromised bone strength. These changes are prevented by ERT with or without progestins. In premenopausal monkeys, bone strength was increased in androgenized animals, with T-treated animals having stronger and denser bones.

EXAMPLE 3

Atherosclerosis-related Studies in Premenopausal Monkeys

The effects of oral contraceptives on CAA of intact female cynomolgus macaques has been investigated (Clarkson, et at, 1990). In this study young adult female cynomolgus macaques were fed an atherogenic diet and divided into 3 groups: a control group, a group given ethinyl estradiol and norgestrel, and another group given ethinyl estradiol and ethynodiol diacetate. Both contraceptive formulations lowered HDL cholesterol. However, the extent of CAA was lessened by both contraceptives.

The inventors have investigated the effects of experimentally induced hyperandrogenism in female monkeys with diet-induced atherosclerosis (Adams, et al., 1995). After 30 months, CAA was almost twice as extensive (p<0.05) in TESTO animals relative to untreated INT animals, while ANDRO treatment had no effect on atherosclerosis extent. The atherogenic effects of T were independent of plasma lipoprotein risk variables. Although atherosclerosis extent was greater in TESTO monkeys, vasomotor activity was similar to that of INT monkeys. The inventors have observed that arterial vasomotion of surgical postmenopausal monkeys was not impaired when methyltestosterone (MT) was added to ethinyl estradiol therapy. MT therapy, therefore, may not suppress the beneficial effects of ethinyl estradiol on the arterial wall (Wagner et al., 1996).

EXAMPLE 4

An oral contraceptive formulation comprising 28 tablets as follows: 6 tablets containing 0.03 mg ethinyl estradiol, 0.05 mg levonorgestrel and 0.25 mg methyltestosterone to be taken on consecutive days 8–13 of a menstrual cycle; 5 tablets containing about 0.075 mg levonorgestrel and about 0.040 mg: ethinyl estradiol to be taken on consecutive days 14–18 of a menstrual cycle; 10 tablets containing about 0.125 mg levonorgestrel and about 0.030 mg ethinyl estradiol to be taken on consecutive days 19–28 of a menstrual cycle; and 7 placebo tablets containing no oral contraceptive hormones to be taken on days 1–7 of the menstrual cycle.

EXAMPLE 5

An oral contraceptive formulation comprising 28 tablets as follows: 6 tablets containing 0.03 mg ethinyl estradiol, 0.05 mg levonorgestrel. and 0.3 mg methyltestosterone to be taken on consecutive days 8–13 of a menstrual cycle; 5 tablets containing about, 0.075 mg levonorgestrel and about 0.040 mg ethinyl estradiol to be taken on consecutive days 14–18 of a menstrual cycle; 10 tablets containing about 0.125 mg levonorgestrel and about 0.030 mg ethinyl estradiol to be taken on consecutive days 19–28 of a menstrual cycle; and 7 placebo tablets containing no oral contraceptive hormones to be taken on days 1–7 of the menstrual cycle.

EXAMPLE 6

An oral contraceptive formulation comprising 28 tablets as follows: 6 tablets containing 0.03 mg ethinyl estradiol, 0.05 mg levonorgestrel and 0.5 mg methyltestosterone to be taken on consecutive days 8–13 of a menstrual cycle; 5 tablets containing about 0.075 mg levonorgestrel, and about 0.040 mg ethinyl estradiol to be taken on consecutive days 14–18 of a menstrual cycle; 10 tablets containing about 0.125 mg levonorgestrel and about 0.030 mg ethinyl estradiol to be taken on consecutive days 9–28 of a menstrual cycle; and 7 placebo tablets containing no oral contraceptive hormones to be taken on days 1–7 of the menstrual cycle.

EXAMPLE 7

An oral contraceptive formulation comprising 28 tablets as follows: 6 tablets containing 0.03 mg ethinyl estradiol, 0.05 mg levonorgestrel and 0.75 mg methyltestosterone to be taken on consecutive days 8–13 of a menstrual cycle; 5 tablets containing about 0.075 mg levonorgestrel and about 0.040 mg ethinyl estradiol to be taken on consecutive days 14–18 of a menstrual cycle; 10 tablets containing about 0.125 mg levonorgestrel and about 0.030 mg ethinyl estradiol to be taken on consecutive days 19–28 of a menstrual cycle; and 7 placebo tablets containing no oral contraceptive hormones to be taken on days 1–7 of the menstrual cycle.

EXAMPLE 8

An oral contraceptive formulation comprising 28 tablets as follows: 6 tablets containing 0.03 mg ethinyl estradiol, 0.05 mg levonorgestrel and 1.0 mg methyltestosterone to be taken on consecutive days 8–13 of a menstrual cycle; 5 tablets containing about 0.075 mg levonorgestrel and about 0.040 mg ethinyl estradiol to be taken on consecutive days 14–18 of a menstrual cycle; 10 tablets containing about 0.125 mg levonorgestrel and about 0.030 mg ethinyl estradiol to be taken on consecutive days 19–28 of a menstrual cycle; and 7 placebo tablets containing no oral contraceptive hormones to be taken on days 1–7 of the menstrual cycle.

EXAMPLE 9

An oral contraceptive formulation comprising 28 tablets as follows: 6 tablets containing 0.03 mg ethinyl estradiol, 0.05 mg levonorgestrel and 1.5 mg methyltestosterone to be taken on consecutive days 8–13 of a menstrual cycle; 5 tablets containing about 0.075 mg levonorgestrel and about 0.040 mg ethinyl estradiol to be taken on consecutive days 14–18 of a menstrual cycle; 10 tablets containing about 0.125 mg levonorgestrel and about 0.030 mg ethinyl estradiol to be taken on consecutive days 19–28 of a menstrual cycle; and 7 placebo tablets containing no oral contraceptive hormones to be taken on days 1–7 of the menstrual cycle.

EXAMPLE 10

An oral contraceptive formulation comprising 28 tablets as follows: 6 tablets containing 0.03 mg ethinyl estradiol, 0.05 mg levonorgestrel and 1.5 mg methyltestosterone to be taken on consecutive days 8–13 of a menstrual cycle; 5 tablets containing about 0.075 mg levonorgestrel and about 0.040 mg ethinyl estradiol to be taken on consecutive days 14–18 of a menstrual cycle; 10 tablets containing about 0.125 mg levonorgestrel and about 0.030 mg ethinyl estradiol to be taken on consecutive days 19–28 of a menstrual cycle; and 7 placebo tablets containing no oral contraceptive hormones to be taken on days 1–7 of the menstrual cycle.

EXAMPLE 11

An oral contraceptive formulation comprising 28 tablets as follows: 6 tablets containing 0.03 mg ethinyl estradiol, 0.05 mg levonorgestrel and 0.25 mg methyltestosterone to be taken on consecutive days 8–13 of a menstrual cycle; 5 tablets containing about 0.075 mg levonorgestrel, about 0.040 mg ethinyl estradiol, and about 0.25 mg methyltestosterone to be taken on consecutive days 14–18 of a menstrual cycle; 10 tablets containing about 0.125 mg levonorgestrel, about 0.030 mg ethinyl estradiol 0.25 mg methyltestosterone to be taken on consecutive days 19–28 of a menstrual cycle; and 7 placebo tablets containing no oral contraceptive hormones to be taken on days 1–7 5 of the menstrual cycle.

EXAMPLE 12

An oral contraceptive formulation comprising 28 tablets as follows: 6 tablets containing 0.03 mg ethinyl estradiol, 0.05 mg levonorgestrel and 0.5 mg methyltestosterone to be taken on consecutive days 8–13 of a menstrual cycle; 5 tablets containing about 0.075 mg levonorgestrel, about 0.040 mg ethinyl estradiol, and about 0.5 mg methyltestosterone to be taken on consecutive days 14–18 of a menstrual cycle; 10 tablets containing about 0.125 mg levonorgestrel, about 0.030 mg ethinyl estradiol 0.5 mg methyltestosterone to be taken on consecutive days 19–28 of a menstrual cycle; and 7 placebo tablets containing no oral contraceptive hormones to be taken on days 1–7 of the menstrual cycle.

While the compositions and methods of this invention have been described in terms of preferred embodiments, it will be apparent to those of skill in the art that variations may be applied to the compositions, methods and in the steps or in the sequence of steps of the methods described herein without departing from the concept, spirit and scope of the invention. More specifically, it will be apparent that certain agents that are both chemically and physically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Adams, Kaplan and Williams, *Arterioscler. Thromb. Vasc. Biol.*, 15:562–570,1995. Adashi, *Fertil. Steril.*, 62:20–27, 1994.

Barrett-Connor, *Am. J Med.*, 98(Suppl. 2A):3S–8S, 1995.

Bubenik, Scharns and Coenen, *Comp. Biochem. Physiol. A Comp. Physiol.*, 87:551–559,1987.

Buchanan, Hospodar, Myers, Levenberger, and Demers, *J Clin. Endocrinol. Metab.*, 67:937–943, 1988.

Carlson, Jayo, Jerome, Register, Weaver and Adams, *Bone Miner.*, 17(Suppl. 1): 151, 1992.

Carlson, Tulli, Jayo, Loeser, Tracy, Mann and Adams, *J Bone Miner. Res.*, 8:71–8 1, 1993.

Carr, Bresau, Givens, Byrd, Bamett-Hamm and Marshbum, *J Clin. Endocrin. Metab.*, 80:1169–1178,1995.

Castro, Rose, Green, Lehner, Peterson and Taub, *Proc. Soc. Exp. BioL Med*, 168:389–394,1981.

Cauley, Gutai, Kuller, Scott and Nevitt, *Am. J Epidemiol.*, 139:1035–1046, 1994.

Clarkson, Shively, Morgan, Koritnik, Adams and Kaplan, *Obstet. Gynecol.*, 75:217–222, 1990.

Cohen-Solal, Shih, Lundy and Parfitt, *J Bone Bone Miner Res.*, 6:1331–1338, 1991.

Colvard, Eriksen, Keeting, Wilson, Lubahn, French, Riggs and Spelsberg, *Proc. Nad. Acad. Sci. USA*, 86:854–857, 1989.

Contraception Report, 6(3):4–14, 1995, anonymous. Cooper, Hannaford, Croft and Kay, *Bone*, 14:41–45, 1993. Corbett, Schey, Lehner and Green, Lab.*Anim.*, 15:3 7–40, 1981. Daniel, Martin and Drinkwater, *Calcif Tissue*

Int., 50:300–305, 1992. Duhper, Warren, Brooks-Gunn and Fox, *J Clin. Endocrinol. Metab.*, 71:1083–1088, 1990. Dupont and Plummer, *Controlled Clin. Trials*, 11: 116–118, 1990.

Flanagan, Lea and Kendall, *J Bone Bone Miner Res.*, 10(Suppl 1):S349, 1995.

Gambacciani, Spinetti, Taponeco, Cappagli, Piaggesi and Fioretti, *Obstet. Gynecol.*, 83:392–396, 1994.

Goldsmith and Johnston, *J Bone J Surg.*, 57A:657–668, 1975.

Goodwin and Jerome, *Lab. Anim. Sci.*, 37:213–216, 1987.

Goulding and Gold, *J Bone Bone Miner Res.*, 8:763–769, 1993.

Greendale, Edelstein and Barrett-Connor, *J Bone Bone Miner Res.*, 10(Suppl. 1I):S263, 1995.

Hansen, *Osteoporosis Int.*, 4:123–128, 1994.

Hanson, Weis, Bolien, Maslan, Singer and Eyre, *J Bone Bone Miner Res.*, 7:1251–1258, 1992.

Hickock, Toomey and Speroff, *Obstet. Gynecol.*, 82:919–924, 1993.

Hughes, Wall, Phil and Creasman, *Gynecol. Oncol.*, 40:42–45, 1991.

Jayo, Weaver, Adams and Rankin, *J Bone Bone Miner Res.*, 4(Suppl ): S 181, 1989.

Jayo, Rankin, Weaver, Carlson and Clarkson, *Calcif Tissue Int.*, 49:438–40,1991.

Jayo, Jerome, Lees, Rankin and Weaver, *Calcif Tissue Int.*, 54:231–6, 1994.

Jayo, Register, Carlson, Rankin, Siew and Sulistiawati, *J Bone Bone Miner Res.*, 10: S256, 1995.

Jerome, Carlson, Register, Bain, Jayo, Weaver and Adams, *J Bone Bone Miner Res.*, 9:527–540, 1994.

Johnston, Longcope and Slemenda, In. *Proceedings of the 4th International Symposium on Osteoporosis and Consensus Development Conference*, B. Riis and C. Christiansen, eds., Copenhagen: Osteopress, 304–305.1993.

Kabcenell, A. I., Pomphrey, A., Barker, D. C., Cox, E., Weisfeld, V. D., Hollendonner, J. K., eds., In. *Challenges in Health Care*, Princeton: The Robert Wood Johnson Foundation, 1991.

Kanders, Lindsay and Dempster, In: *Osteoporosis*, Proceedings of the International Symposium on Osteoporosis, C. Christiansen, C. D. Arnaud, B E C Nordin, A. M. Parfitt, W. A. Peck, B. L. Riggs, eds., Copenhagen: Osteopress, pp. 337–339, 1984.

Kanders, Dempster and Lindsay, *J Bone Bone Miner Res.*, 3:145–149, 198 8.

Kanis, *Am. J Med*, 98(Suppl. 2A):605–665, 1995.

Kasperk, Fitzsimmonds, Strong, Mohan, Jennings, Wegedal and Baylink, *J Clin. Endocrinol. Metab.*, 71:1322–1329, 1990.

Kasra and Grynpas, *Trans. ORS*, 2(17):544, 1992.

Kasra and Grynpas, Bone, 17:265–270, 1995.

Kulin, In: *Rudolph's Pediatrics*, 19th edition, A. M. Rudolf, J. I. E. Horman, C. D. Rudolph, eds., Norwalk, Conn.: Appleton and Lange, pp. 1665–1668, 1991.

Kuhnz, Staks and Juetting, *Contraception*, 50:563–580, 1994.

Lea, Moxharn and Flanagan, *J Bone Bone Miner Res.*, 10(Suppl. 1):S349, 1995.

Lindsay, Tohme and Kanders, *Contraception*, 34:333–340, 1986.

Lindsay, *Am. J Med*, 98(Suppl. 2A):9S–1 IS, 1995.

Looker, Johnston, Wahner, Dunn, Calvo, Harris, Heyse and Lindsay, *J Bone Bone Miner Res.*, 10:796–802, 1995.

MacCann and Potter, *Contraception*, 50(Suppl. 1):S1–S198, 1994.

Mahoney, *J Reprod. Fertil.*, 21:153–163, 1970.

Mais, Fruzzetti, Ajossa, Paoletti, Guerriero and Melis, *Contraception*, 48:445–452, 1993.

Matkovic, Jelic, Wardlaw, Rich, Goel, Wright, Andon, Smith and Heaney, *J Clin. Invest.*, 93:799–808, 1994.

Mazess and Barden, *Am. J Clin. Nutr.*, 53:132–142, 1991.

Meikle et al., *J Clin Endocrinol Metab* 74:623–8, 1992.

Melton, *J Bone Bone Miner Res.*, 10: 175–177, 1995.

Munoz-Torres, Quesada and Escobar-Jimenez, *Calcif Tissue Int.*, 30 57:94–96, 1995.

Parfitt, Simon, Villanueva and Krane, *J. Bone Miner. Res.*, 2:427–43 6, 1987a.

Parfitt, Drezner, Glorieux, Kanis, Malluche, Meunier, Ott and Recker, *J Bone Bone Miner Res.*, 2:595–610, 1987b.

Pincus, In: Clinical Endocrinology I, E. B. Astwood, ed., Gfune & Stratton, Inc., New York, pp. 526–531, 1960.

Raisz, et al. *Journal of Clinical Endocrinology and Metabolism*, 81: 37–43, 1996. Recker, Davies, Hinders, Heaney, Stegman and Kimmel, *JAMA*, 268:2403–2408, 1992.

Register, Jayo and Jerome, *J Bone Min. Reser.*, 10(Suppl 1):S, 1995.

Rock, Garcia and Pincus, *Recent Prog Horm. Res.*, 13:323–339, 1957.

Rosenfield and Lucky, *Endocrinol. Metabol. Clin. North Am.*, 22:507–532,1993.

Shively, Jayo, Weaver and Kaplan, *Arteriosclerosis*, 7:226–231, 1987.

Siegel, In: Nomparametric statistics for behavioral sciences, New York: McGraw-Hill, 1956.

Sokal R R, Rohlf F J., eds. Biometry, 2nd ed. New York: W.H. Freeman & Co., 1981:262–264.

Speroff and Damey, In. *A Clinical Guide for Contraception*, Baltimore: Williams and Wilkins, 1992.

Stevenson, Lees, Devenport, Cust and Ganger, *Br. Med J*, 298:924–8, 1989.

Takeuchi and Guggino, *J Bone Min. Res.*, 10(Suppl. 1): S497, 1995.

Teegarden, Lyle, Proulx, Kern, McCabe, Peacock, Johnston and Weaver, *J Bone Miner.* Res., 10(Suppl 1): S456, 1995.

Tulli, Carlson, Jayo, Fisher, Tracy and Mann, *J Histotechnol.*, 15:93–97, 1992.

Tuppurainen, Kroger, Saarikoski, Honkanen and Alhava, *Osteoporosis International*, 4:93–98, 1994.

Vanin, Lammers, MacLusky, Casper and Grynpas, *J Bone Bone Miner Res.*, 10(Suppl. 1): S250, 1995.

Wagner J. D. et al., *Arteriosclerosis, Thrombosis & Vascular Biology* 16:1473–80, 1996.

Watts, Notelovitz, Timmons, Addison, Wiita and Downey, *Obstet. Gynecol*, 85:529–537, 1995.

Wiegratz, Jung-Hoffmann and Kuhl, *Contraception*, 51:341–346, 1995.

Wilson, Gordon and Collins, *Biol. Reprod.*, 27:530–539, 1982.

Wiren, Keenan and Orwoll, *J Bone Bone Miner Res.*, 10(Suppl. 1): S494, 1995.

Wright, Papadea, Willi, Pandey, Key and Bell, *J Bone Bone Miner Res.*, 10(Suppl. 1):S447, 1995.

Yamamoto and Okada, *Asia-Oceania J Obstet. Gynaecol.*, 20:225–230, 1994. Yu et al., *J Clin Pharmacol* 37:1139–45, 1997.

What is claimed is:

1. A pharmaceutical composition for contraception or hormone replacement therapy, said composition comprising a hormonal component, wherein the hormonal component consists of an estrogen, a progestin and an androgen, and wherein the estrogen concentration is from about 5 micrograms to about 35 micrograms per daily dose.

2. The composition of claim 1, wherein the estrogen is ethinyl estradiol.

3. The composition of claim 2, wherein the ethinyl estradiol component is about 15 micrograms per daily dose.

4. The composition of claim 2, wherein the ethinyl estradiol component is about 10 micrograms per daily dose.

5. The composition of claim 2, wherein the ethinyl estradiol component is about 5 micrograms per daily dose.

6. The composition of claim 1, wherein said androgen is methyltestosterone.

7. The composition of claim 6, comprising from about 0.1 milligrams to about 1.5 milligrams methyltestosterone per daily dose.

8. The composition of claim 1, wherein said progestin is from about 0.030 milligrams to about 0.2 milligrams levonorgestrel per daily dose.

9. The composition of claim 1, wherein said composition comprises a tablet for oral administration.

10. The composition of claim 1, wherein said composition comprises a topical ointment.

11. The composition of claim 1, wherein said composition comprises a skin patch.

12. The composition of claim 1, wherein said composition is administered to a fertile female on about days 8–13 of a menstrual cycle.

13. The composition of claim 1, wherein said composition is adminstered to a female during menopause.

14. The composition of claim 1, wherein said composition is adminstered to an infertile female in need thereof.

15. A pharmacetical composition comprising a hormonal component, wherein the hormonal component consists essentially of:

an estrogen having estrogenic activity equivalent to from about 5 micrograms to about 35 micrograms ethinyl estradiol;

a progestin having progestogenic activity equivalent to from about 0.030 milligrams to about 0.2 milligrams levonorgestrel; and an androgen having androgenic activity equivalent to from about 0.1 1milligrams to about 1.5 milligrams methyltestosterone per daily dose.

16. The composition of claim 15, wherein said estrogen is selected from the group consisting of 5 micrograms, 10 micrograms, 20 micrograms and 30 micrograms ethinyl estradiol.

17. The composition of claim 15, wherein said progestin is selected from the group consisting of 50 micrograms, 100 micrograms and 150 micrograms levonorgestrel.

18. The composition of claim 15, wherein said androgen is selected from the group consisting of 0.25 milligrams, 0.5 milligrams, 0.75 milligrams and 1.5 milligrams methyltestosterone.

19. A pharmaceutical composition comprising 5 micrograms ethinyl estradiol, 25 micrograms levonorgestrel and 0.25 milligrams methyltestosterone per daily dose.

20. A pharmaceutical composition comprising 5 micrograms ethinyl estradiol, 50 micrograms levonorgestrel and 0.5 milligrams methyltestosterone per daily dose.

21. A pharmaceutical composition comprising 10 micrograms ethinyl estradiol, 50 micrograms levonorgestrel and 0.5 milligrams methyltestosterone per daily dose.

22. A pharmaceutical composition comprising 10 micrograms ethinyl estradiol, 100 micrograms levonorgestrel and 1 milligram methyltestosterone per daily dose.

23. A pharmaceutical composition comprising 20 micrograms ethinyl estradiol, 100 micrograms levonorgestrel and 0.5 milligrams methyltestosterone per daily dose.

24. A pharmaceutical composition comprising 20 micrograms ethinyl estradiol, 100 micrograms levonorgestrel and 1 milligram methyltestosterone per daily dose.

25. An oral contraceptive preparation comprising:

(a) a composition comprising methyltestosterone, levonorgestrel and from about 5 to about 18 micrograms of ethinyl estradiol to be administered daily on consecutive days of a portion of a menstrual cycle; and (b) a composition comprising levonorgestrel and ethinyl estradiol to be administered daily on consecutive days of a portion of a menstrual cycle.

26. The preparation of claim 25, wherein the composition of (a) is further defined as comprising about 0.2 mg to about 1.5 mg methyltestosterone per daily dose.

27. The preparation of claim 25, wherein the composition of (a) is further defined as comprising about 0.050 mg levonorgestrel per daily dose.

28. The preparation of claim 25, wherein the composition of (b) is further defined as comprising from about 0.05 to about 0.125 milligrams of levonorgestrel per daily dose.

29. A method of replacing the natural estrogen to androgen balance in a female in need of estrogen therapy, wherein the method comprises administering to the female a pharmaceutical composition comprising a hormonal component, wherein the hormones in the hormonal component are from about 5 to about 30 micrograms of ethinyl estradiol per dialy dose, a progestin and an androgen.

30. The method of claim 29, wherein the estrogen therapy is a contraceptive.

31. The method of claim 29, wherein the estrogen therapy is due to a loss or change in ovarian secretion of an estrogen, an androgen, an estrogen precursor or an androgen precursor.

32. The method of claim 29, wherein the hormonal component includes from about 0.2 mg to about 1.5 mg methyltestosterone per daily dose.

33. The method of claim 29, wherein the composition is administered orally.

34. The method of claim 29, wherein the composition is administered subdermally.

35. The method of claim 29, wherein the composition is administered transdermally.

36. The method of claim 29, wherein the female has not attained peak bone mass.

37. The method of claim 29, wherein the female is remenopausal.

38. The method of claim 29, wherein the female has a loss or change in ovarian secretion of an estrogen, an androgen, an estrogen precursor or an androgen precursor.

39. The method of claim 29, wherein the female has a loss or change in ovarian secretion of an estrogen, an androgen, an estrogen precursor or an androgen precursor due to menopause.

* * * * *

UNITED STATES PATENT AND TRADEMARK OFFICE
CERTIFICATE OF CORRECTION

PATENT NO. : 6,139,873
DATED : October 31, 2000
INVENTOR(S) : Claude L. Hughes and Manuel J. Jayo It is certified that error appears in the above-identified patent and that said Letters Patent are hereby corrected as shown below:

In column 38, Claim 37, line 53 delete the term "remenopausal" and insert therefor --premenopausal--.

Signed and Sealed this

Twenty-second Day of May, 2001

Attest:

NICHOLAS P. GODICI

Attesting Officer

Acting Director of the United States Patent and Trademark Office